US009550728B2

(12) United States Patent
Lee et al.

(10) Patent No.: US 9,550,728 B2
(45) Date of Patent: Jan. 24, 2017

(54) THERMO-RESPONSIVE DRAW SOLUTE FOR FORWARD OSMOSIS AND METHOD FOR WATER DESALINATION AND PURIFICATION USING THE SAME

(75) Inventors: Yan Lee, Seoul (KR); Minwoo Noh, Seoul (KR); Yeongbong Mok, Gyeongsangnam-do (KR); Heejin Kim, Gyeonggi-do (KR); Seonju Lee, Chungcheongbuk-do (KR); Daichi Nakayama, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 277 days.

(21) Appl. No.: 14/235,192

(22) PCT Filed: Jul. 27, 2012

(86) PCT No.: PCT/KR2012/006017
§ 371 (c)(1),
(2), (4) Date: Jan. 27, 2014

(87) PCT Pub. No.: WO2013/015651
PCT Pub. Date: Jan. 31, 2013

(65) Prior Publication Data
US 2014/0158621 A1 Jun. 12, 2014

(30) Foreign Application Priority Data

Jul. 27, 2011 (KR) .................... 10-2011-0074786

(51) Int. Cl.
*B01D 11/00* (2006.01)
*C02F 1/44* (2006.01)
(Continued)

(52) U.S. Cl.
CPC ........... *C07C 233/05* (2013.01); *B01D 61/002* (2013.01); *B01D 61/005* (2013.01); *C02F 1/445* (2013.01);
(Continued)

(58) Field of Classification Search
CPC . B01D 61/002; B01D 63/00; B01D 2311/103; B01D 2311/06

USPC ......................................................... 210/644
See application file for complete search history.

(56) References Cited

U.S. PATENT DOCUMENTS

| 3,532,621 A | * | 10/1970 | Hough | B01D 61/002 210/638 |
| 4,968,453 A | * | 11/1990 | Wada | C10M 111/04 508/485 |
| 7,560,029 B2 | * | 7/2009 | McGinnis | B01D 61/002 210/644 |

(Continued)

FOREIGN PATENT DOCUMENTS

| JP | 2010274252 | 12/2010 |
| KR | 101011403 | 1/2011 |

(Continued)

OTHER PUBLICATIONS

Service, Robert F., "Desaination Freshens Up;" AAAS, Science, Aug. 25, 2006, vol. 313, pp. 1088-1090.

*Primary Examiner* — Ana Fortuna
(74) *Attorney, Agent, or Firm* — Duane Morris LLP; J. Rodman Steele, Jr.; Gregory M. Lefkowitz

(57) ABSTRACT

The present invention relates to a thermo-responsive draw solute that can be applied to water desalination and purification based on forward osmosis. The thermo-responsive draw solute has a molar mass of 50 to 3000 g/mol and undergoes a phase transition at a temperature of 0° C. to 70° C. The thermo-responsive draw solute creates optimum conditions for the desalination of seawater and the purification of contaminated water based on forward osmosis. The present invention also relates to a method for water desalination and purification using the thermo-responsive draw solute. The method consumes little energy for water desalination or purification, is simple to apply to water desalination or purification, and enables separation of the draw solute in a very easy manner.

14 Claims, 14 Drawing Sheets

(51) Int. Cl.
*B01D 61/00* (2006.01)
*B01D 61/24* (2006.01)
*C07C 233/05* (2006.01)
*C07C 233/36* (2006.01)
*C07C 309/14* (2006.01)
*C02F 103/08* (2006.01)

(52) U.S. Cl.
CPC ........... *C07C 233/36* (2013.01); *C07C 309/14* (2013.01); *C02F 2103/08* (2013.01); *C02F 2303/18* (2013.01); *Y02W 10/37* (2015.05)

(56) References Cited

U.S. PATENT DOCUMENTS

| | | | |
|---|---|---|---|
| 7,914,680 B2* | 3/2011 | Cath | B01D 61/002 203/10 |
| 2005/0059841 A1* | 3/2005 | Drent | C07C 51/56 562/890 |
| 2006/0226067 A1 | 10/2006 | Herron | |
| 2011/0203994 A1* | 8/2011 | McGinnis | B01D 61/002 210/650 |
| 2012/0114745 A1* | 5/2012 | Pui | A61K 9/0014 424/450 |
| 2012/0279921 A1* | 11/2012 | Nicoll | B01D 61/002 210/648 |

FOREIGN PATENT DOCUMENTS

| | | |
|---|---|---|
| KR | 1020110067748 | 6/2011 |
| KR | 1020110091153 | 11/2011 |
| WO | WO 2014/175833 | * 10/2014 |

* cited by examiner

THERMO-RESPONSIVE DRAW SOLUTE FOR FORWARD OSMOSIS AND METHOD FOR WATER DESALINATION AND PURIFICATION USING THE SAME

CROSS-REFERENCE TO RELATED APPLICATIONS

This application is a §371 national stage entry of International Application No. PCT/KR2012/006017, filed Jul. 27, 2012, which claims priority to Korean Patent Application No. 10-2011-0074786 filed Jul. 27, 2011, the entire contents of which are incorporated herein by reference.

TECHNICAL FIELD

The present invention relates to a draw solute that can be applied to water desalination and purification based on forward osmosis, and a method for water desalination and purification using the draw solute.

BACKGROUND ART

Water shortage is now a growing global concern. The supply of water resources does not keep pace with an increasing demand and the contamination of water leads to the deficiency of available water. At present, roughly one third of the world's population lives in areas that lack water. It is estimated that about two third of the world's population will suffer from water shortage by 2020 (R. F. Service, Science 313, 1088 (2006)). Under such circumstances, considerable research efforts have been made to produce clean water by desalinating or purifying seawater, river water, and contaminated water.

Established commercial techniques for producing clean water are, for example, based on distillation and reverse osmosis using semi-permeable membranes through which particles other than water do not pass. However, according to the distillation, boiling water consumes energy as much as 10-16 kWh/m$^3$. According to the reverse osmosis, much energy is needed (4-6 kWh/m$^3$) because a pressure should be applied that is greater than the osmotic pressure of a solution to be removed.

Forward osmosis (FO) has recently received attention as future technology for water desalination and purification due to its higher energy efficiency than distillation and reverse osmosis. Forward osmosis is performed in two steps. In the first step, a water species requiring desalination or purification and a solution having a higher osmotic pressure than the water species are arranged to face each other through a semi-permeable membrane. This solution is referred to as a "draw solution" and a constituent solute of the draw solution is referred to as a "draw solute." With this arrangement, water migrates to the draw solution by osmosis even without additional energy supply. In the subsequent second step, the solute is technically removed from the draw solution that has drawn the water. According to the forward osmosis, clean water can be obtained even by very low energy consumption.

The choice of a suitable draw solute having an optimum osmotic pressure and the removal of the draw solute from clean water after desalination or purification are key considerations in forward osmosis. Ammonium bicarbonate ($NH_4HCO_3$) is currently the most widely studied draw solute in forward osmosis. Ammonium bicarbonate is dissociated into ammonium ($NH_4^+$) and bicarbonate ($HCO_3^-$) ions. A high concentration solution of ammonium bicarbonate can draw water from seawater, river water, and contaminated water through osmosis due to its high osmotic pressure. After water has been drawn using ammonium bicarbonate, heat at 60° C. is supplied to remove the solute. The heat vaporizes the solute ammonium bicarbonate into ammonia ($NH_3$) and carbon dioxide ($CO_2$). As a result, the water solubility of the gases is extremely lowered, enabling the production of clean water.

However, several limitations exist in forward osmosis using ammonium bicarbonate. First, there is a risk that the basic ammonium bicarbonate solution may damage the physical properties of semi-permeable membranes typically composed of polymeric materials. Another limitation is that high energy is still needed to reach a temperature (60° C.) for removal of the solute. Besides maintaining the temperature at 60° C., removal of the draw solute requires the use of a complex column distillation process, which is also a disadvantage of forward osmosis. Another problem of forward osmosis is that the reuse of the draw solute involves a complicated process.

In this connection, Korean Patent Publication No. 2011-0091153 discloses a draw solution for forward osmosis. Specifically, the draw solution is an aqueous solution containing a draw solute in the form of a salt consisting of an anion and a cation, typically an ammonium ion. The draw solute is vaporized and separated from the aqueous solution. However, the inherent problems of forward osmosis using ammonium bicarbonate remain unsolved and the consumption of high energy is needed to reach a high temperature of 40° C. to 90° C., which is much higher than room temperature.

Despite many efforts to solve the disadvantages of the prior art, any of the draw solutes proposed to date is still unsatisfactory. Thus, there is a need to develop a new concept of draw solute and a forward osmosis system using the draw solution.

DISCLOSURE

Technical Problem

Therefore, the present invention is intended to provide a thermo-responsive draw solute for forward osmosis that creates optimum conditions for the desalination of seawater and the purification of contaminated water based on forward osmosis, and a method for water desalination and purification using the thermo-responsive draw solute that consumes little energy for water desalination or purification, is simple to apply to water desalination or purification, and enables separation of the draw solute in a very easy manner.

Technical Solution

A first aspect of the present invention provides a thermo-responsive draw solute for forward osmosis that has a molar mass of 50 to 3000 g/mol and undergoes a phase transition at a temperature of 0° C. to 70° C.

According to one embodiment of the present invention, the phase transition may occur at a temperature higher than a lower critical solution temperature.

According to an alternative embodiment of the present invention, the phase transition may occur at a temperature lower than an upper critical solution temperature.

According to another embodiment of the present invention, the draw solute undergoing a phase transition at a temperature higher than a lower critical solution temperature may be selected from the group consisting of:

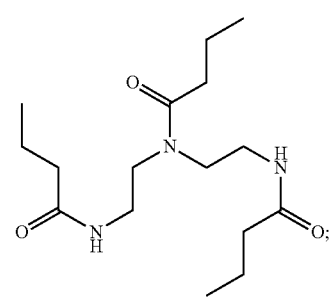

N,N-bis(2-butyramidoethyl)butyramide
(nBu-DETA)

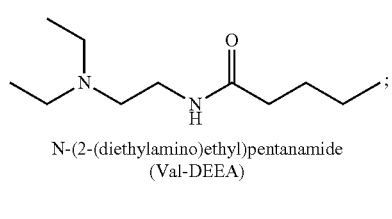

N-(2-(diethylamino)ethyl)pentanamide
(Val-DEEA)

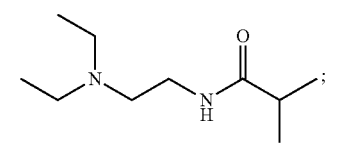

N-(2-(diethylamino)ethyl)isobutyramide
(iBu-DEEA)

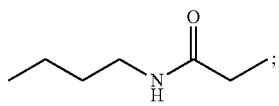

N-butylpropionamide (N-BPA)

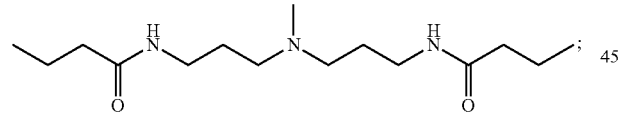

N,N'-((methylazanediyl)bis(propan-3,1-diyl)dibutyramide (nBu-DAPMA)

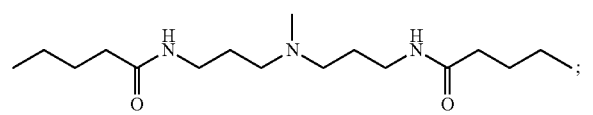

N,N'-((methylazanediyl)bis(propan-3,1-diyl)dipentanamide (Val-DAPMA)

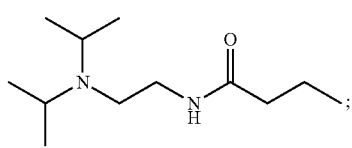

N-(2-(diisopropylamino)ethyl)butyramide
(n-Bu-DIPA)

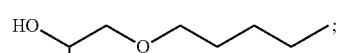

propylene glycol pentyl ether (PNP)

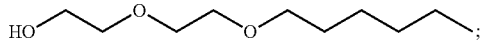

di(ethylene glycol)hexyl ether (DEH)

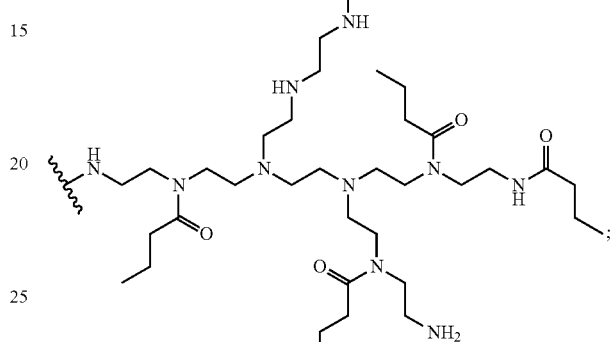

butyrylated polyethyleneimine (nBu-PEI)

and mixtures thereof.

According to another embodiment of the present invention, the draw solute undergoing a phase transition at a temperature lower than an upper critical solution temperature may be selected from the group consisting of:

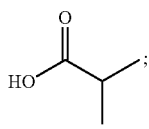
isobutyric acid
(IBA)

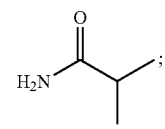
isobutyramide acid
(IBAm)

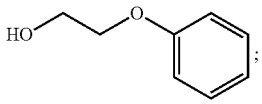

ethylene glycol monophenyl ether
(EGPE)

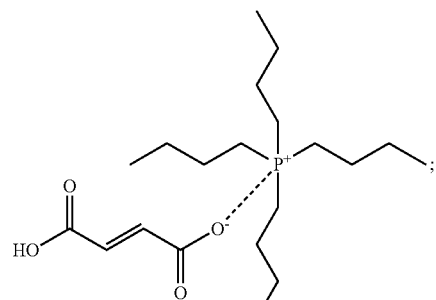

tetra-n-butylphosphonium fumarate (P4BF)

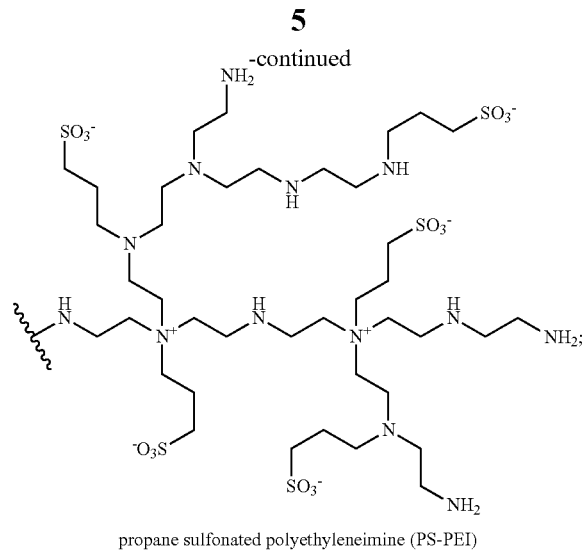

propane sulfonated polyethyleneimine (PS-PEI)

and
mixtures thereof.

One embodiment of a second aspect of the present invention provides a method for water desalination and purification using a thermo-responsive draw solute for forward osmosis, the method including:

1) bringing unpurified water into contact with a draw solution including the thermo-responsive draw solute at a higher concentration than the unpurified water through a semi-permeable membrane;

2) allowing clean water to flow from the unpurified water into the draw solution through the semi-permeable membrane by forward osmosis;

3) raising the temperature of the draw solution to or above the critical solution temperature of the thermo-responsive draw solute to cause a phase transition of the thermo-responsive draw solute from the draw solution; and 4) separating the clean water from the draw solution.

According to one embodiment of the present invention, the thermo-responsive draw solute for forward osmosis has a molar mass of 50 to 3000 g/mol and undergoes a phase transition at a temperature of 0° C. to 70° C.

According to a further embodiment of the present invention, the thermo-responsive draw solute for forward osmosis may be selected from the group consisting of:

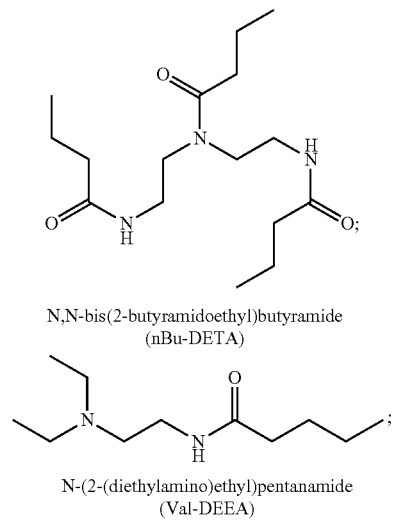

N,N-bis(2-butyramidoethyl)butyramide (nBu-DETA)

N-(2-(diethylamino)ethyl)pentanamide (Val-DEEA)

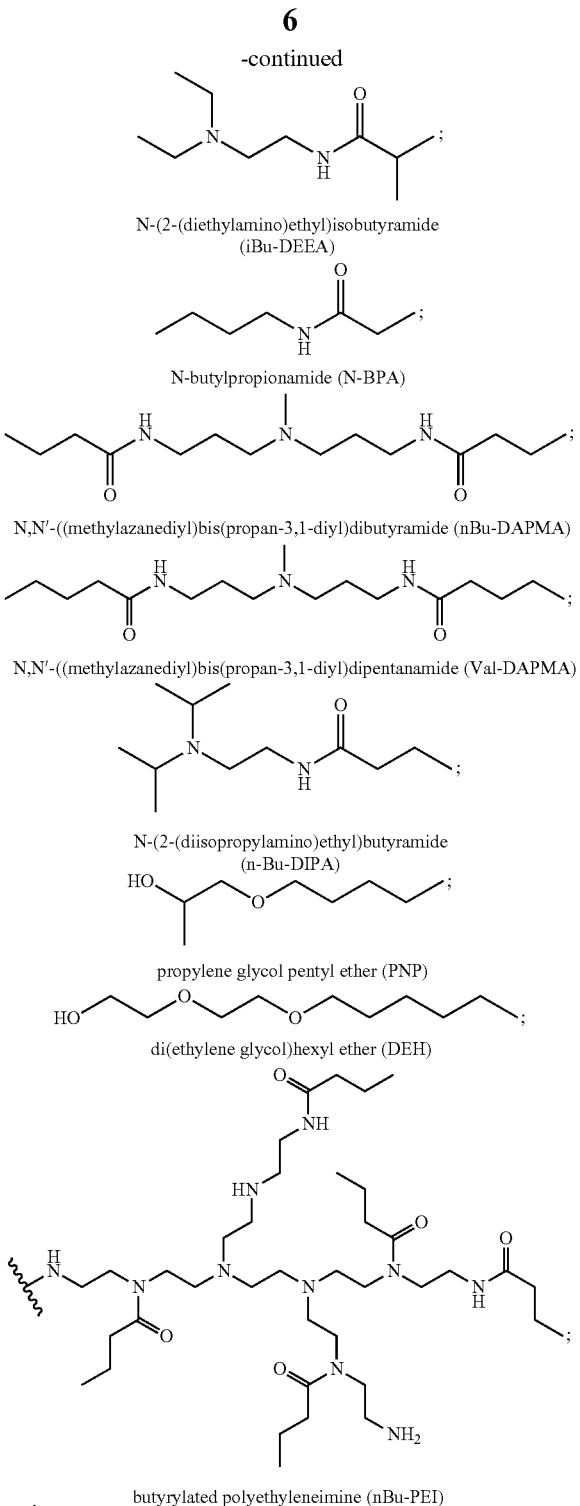

N-(2-(diethylamino)ethyl)isobutyramide (iBu-DEEA)

N-butylpropionamide (N-BPA)

N,N'-((methylazanediyl)bis(propan-3,1-diyl)dibutyramide (nBu-DAPMA)

N,N'-((methylazanediyl)bis(propan-3,1-diyl)dipentanamide (Val-DAPMA)

N-(2-(diisopropylamino)ethyl)butyramide (n-Bu-DIPA)

propylene glycol pentyl ether (PNP)

di(ethylene glycol)hexyl ether (DEH)

butyrylated polyethyleneimine (nBu-PEI)

and
mixtures thereof.

According to another embodiment of the present invention, the semi-permeable membrane may be a cellulose acetate or polyether sulfone semi-permeable membrane.

According to another embodiment of the present invention, the unpurified water may be water including ions, colloids, microbes, water soluble molecules, insoluble organic molecules, or mixtures thereof.

A further embodiment of the second aspect of the present invention provides a method for water desalination and purification using a thermo-responsive draw solute for forward osmosis, the method including:

1) bringing unpurified water into contact with a draw solution including the thermo-responsive draw solute at a higher concentration than the unpurified water through a semi-permeable membrane;

2) allowing clean water to flow from the unpurified water into the draw solution through the semi-permeable membrane by forward osmosis;

3) raising the temperature of the draw solution to or below the critical solution temperature of the thermo-responsive draw solute to cause a phase transition of the thermo-responsive draw solute from the draw solution; and 4) separating the clean water from the draw solution.

According to one embodiment of the present invention, the thermo-responsive draw solute has a molar mass of 50 to 3000 g/mol and undergoes a phase transition at a temperature of 0° C. to 70° C.

According to a further embodiment of the present invention, the thermo-responsive draw solute may be selected from the group consisting of:

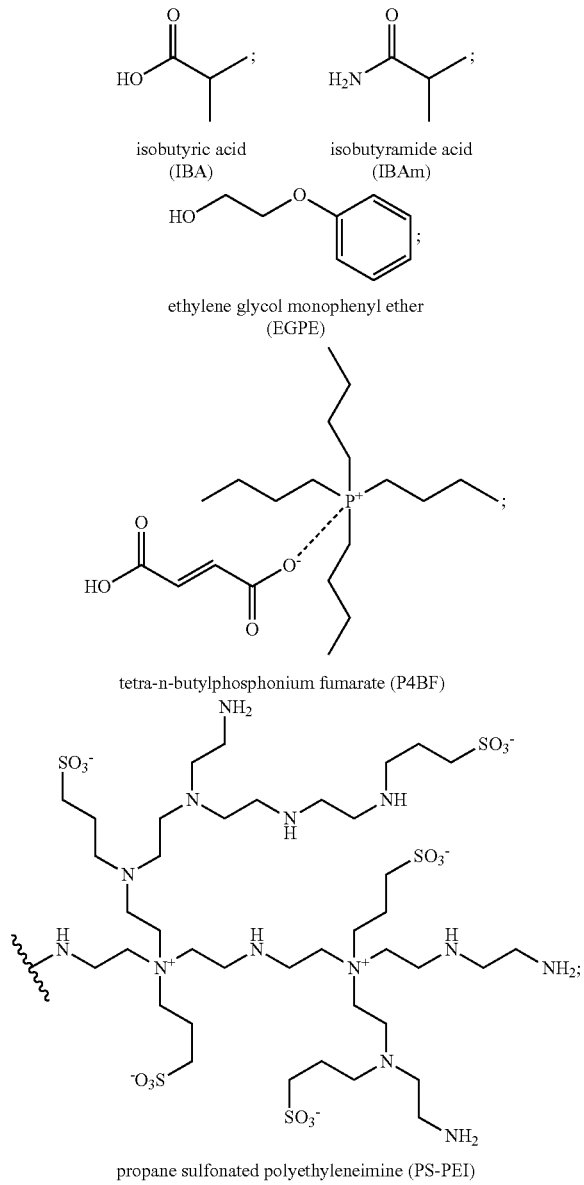

isobutyric acid (IBA)

isobutyramide acid (IBAm)

ethylene glycol monophenyl ether (EGPE)

tetra-n-butylphosphonium fumarate (P4BF)

propane sulfonated polyethyleneimine (PS-PEI)

and mixtures thereof.

According to another embodiment of the present invention, the semi-permeable membrane may be a cellulose acetate or polyether sulfone semi-permeable membrane.

According to another embodiment of the present invention, the unpurified water may water including ions, colloids, microbes, water soluble molecules, insoluble organic molecules, or mixtures thereof.

Advantageous Effects

The thermo-responsive draw solute for forward osmosis according to the present invention creates optimum conditions for the desalination of seawater and the purification of contaminated water based on forward osmosis. In addition, the water desalination and purification method of the present invention consumes little energy for water desalination or purification, is simple to apply to water desalination or purification, and enables separation of the draw solute in a very easy manner.

BEST MODE

Exemplary embodiments of the present invention will now be described in more detail with reference to the accompanying drawings.

Figure 1:
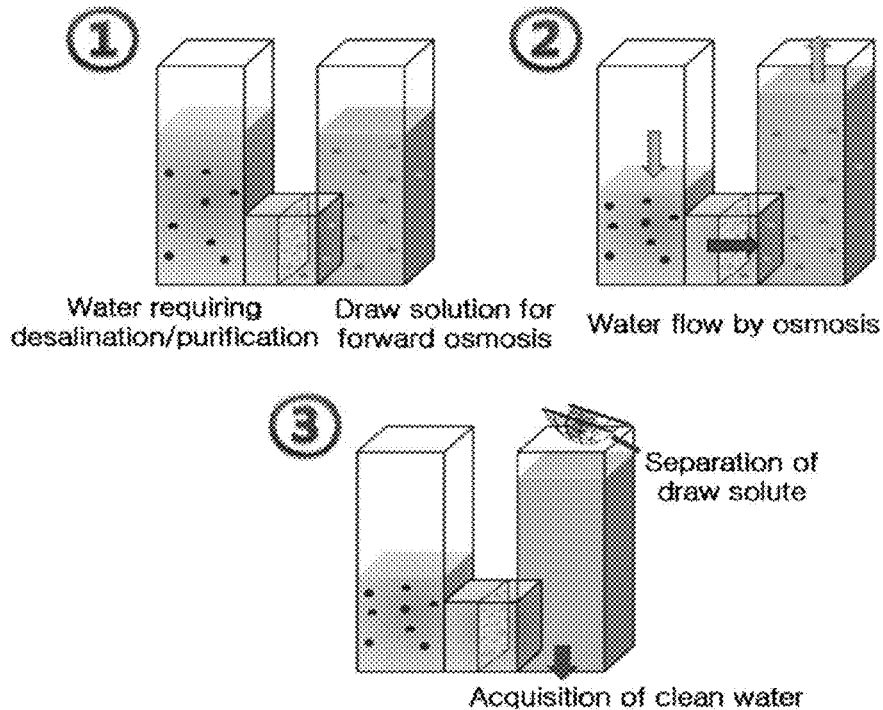
FIG. 1 is a schematic process diagram of a conventional method for water desalination and purification based on forward osmosis.

FIG. 1 is a schematic process diagram of a conventional method for water desalination and purification based on forward osmosis. Referring to FIG. 1, unpurified water is arranged at one side of a semi-permeable membrane and a draw solution having a higher osmotic pressure than the unpurified water is arranged at the other side of the semi-permeable membrane (step ① of FIG. 1). With this arrangement, water is allowed to migrate from the unpurified water having a lower osmotic pressure to the draw solution having a higher osmotic pressure (step ② of FIG. 1). Finally, a draw solute is separated from the draw solution to obtain purified clean water (step ③ of FIG. 1).

Unlike the draw solute used in the conventional water purification method based on forward osmosis, a thermo-responsive draw solute undergoing a phase transition at a particular temperature is used in the present invention. The term "thermo-responsive (or thermo-sensitive)" as used herein means a property of the draw solute in which when the molar fraction of the draw solute in an aqueous solution is below a predetermined level, the aqueous solution exists in a homogeneous state in the temperature range higher or lower than the reference temperature but the solubility of the draw solute in the solution drops sharply in the opposite temperature range, leading to a phase transition of the draw solute.

The thermo-responsive property is broadly classified into two types: lower critical solution temperature (LCST) and upper critical solution temperature (UCST) types. In the LCST type, the draw solute forms a homogeneous phase at a temperature lower than the reference temperature and undergoes a phase transition at a temperature higher than the reference temperature. In the UCST type, the draw solute forms a homogeneous phase at a temperature higher than the reference temperature and undergoes a phase transition at a temperature lower than the reference temperature. The reference temperature is also called a "phase transition temperature."

In the present invention, such thermo-responsive compounds are used as draw solutes for forward osmosis. Thermo-responsive compounds having a molar mass of 50 to 3000 g/mol and undergoing a phase transition at 0° C. to 70° C. are particularly suitable for use as draw solutes for forward osmosis. Another requirement of suitable draw solutes for forward osmosis is a low molecular weight or molar mass due to the necessity of high osmotic pressure. A preferred molar mass is preferably in the range of 50 to 3000 g/mol. At a molar mass lower than 50 g/mol, the possibility is low that a thermo-responsive phase transition may occur and the possibility is high that the molecules may pass through semi-permeable membranes due to their small particle size.

An advantage of forward osmosis over distillation or reverse osmosis is that water can be desalinated and purified without additional energy supply. This advantage is achieved when a phase transition occurs at a relatively low reference temperature, preferably between 0° C. and 70° C.

As described above, a draw solution having lower critical solution temperature characteristics may undergo a phase transition at a temperature higher than the lower critical solution temperature from a homogeneous phase at a temperature lower than the lower critical solution temperature. Alternatively, a draw solution having upper critical solution temperature characteristics may undergo a phase transition at a temperature lower than the upper critical solution temperature from a homogeneous phase at a temperature higher than the upper critical solution temperature. In the lower critical solution temperature type phase transition, the reference temperature, at which the phase transition occurs, may be in the range of 0° C. to 70° C., as described above.

In the present invention, specific compounds capable of meeting the above requirements were newly synthesized and some commercially available compounds capable of meeting the above requirements were searched.

Specific examples of the compounds undergoing a phase transition at a temperature higher than a lower critical solution temperature include:

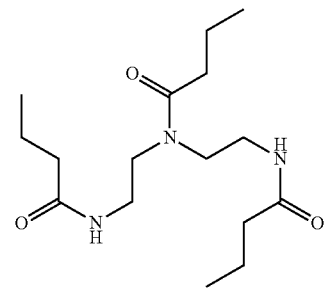

N,N-bis(2-butyramidoethyl)butyramide (nBu-DETA)

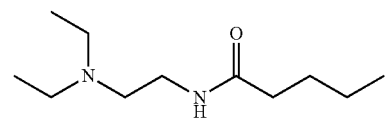

N-(2-(diethylamino)ethyl)pentanamide (Val-DEEA)

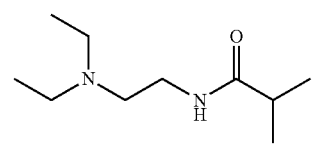

N-(2-(diethylamino)ethyl)isobutyramide (iBu-DEEA)

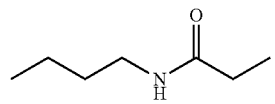

N-butylpropionamide (N-BPA)

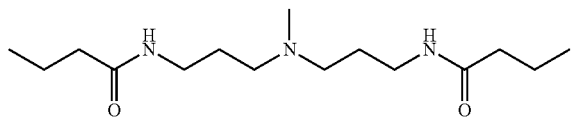

N,N'-((methylazanediyl)bis(propan-3,1-diyl)dibutyramide (nBu-DAPMA)

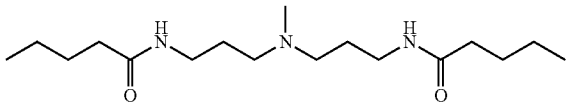

N,N'-((methylazanediyl)bis(propan-3,1-diyl)dipentanamide (Val-DAPMA)

-continued

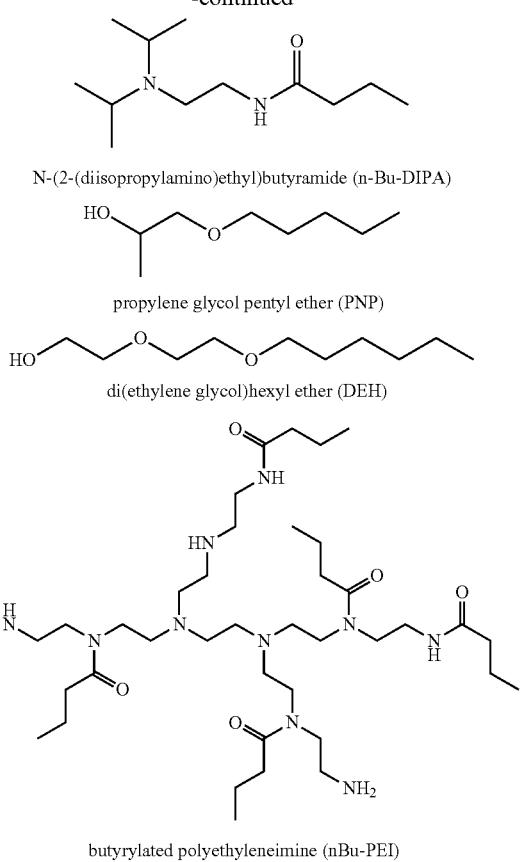

N-(2-(diisopropylamino)ethyl)butyramide (n-Bu-DIPA)

propylene glycol pentyl ether (PNP)

di(ethylene glycol)hexyl ether (DEH)

butyrylated polyethyleneimine (nBu-PEI)

Examples of the compounds undergoing a phase transition at a temperature lower than an upper critical solution temperature include:

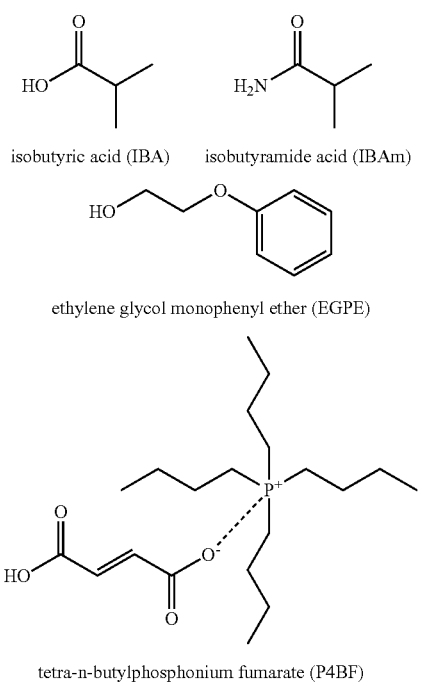

isobutyric acid (IBA)   isobutyramide acid (IBAm)

ethylene glycol monophenyl ether (EGPE)

tetra-n-butylphosphonium fumarate (P4BF)

-continued

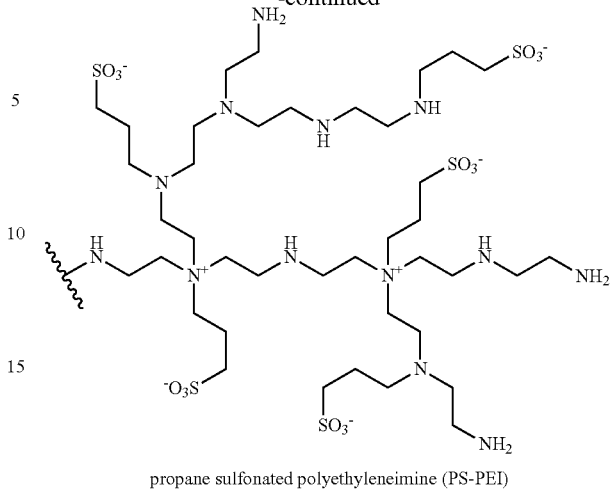

propane sulfonated polyethyleneimine (PS-PEI)

Figure 2:
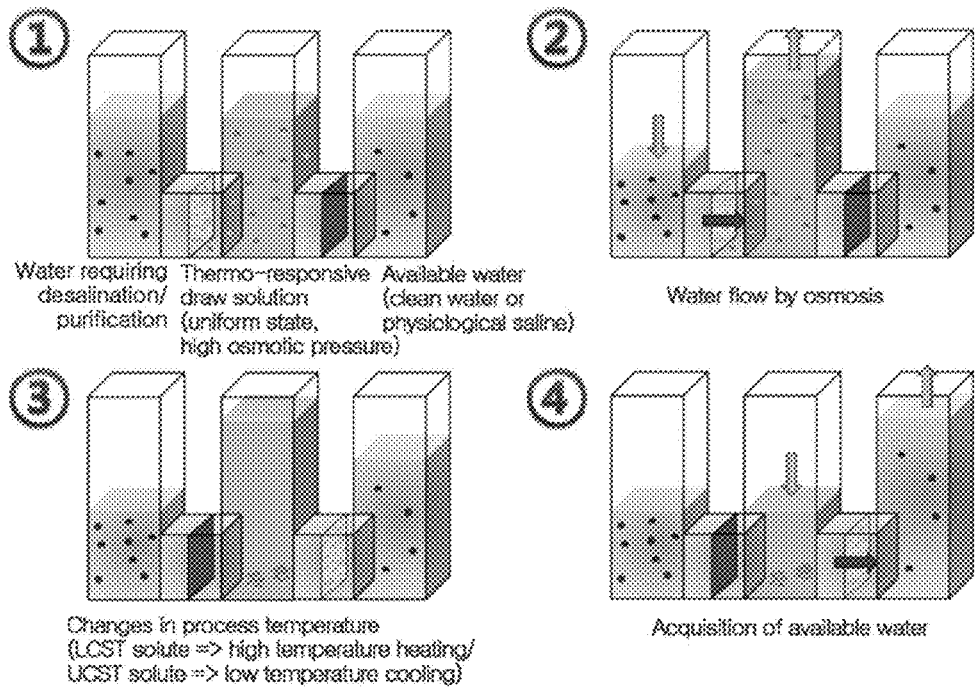
FIG. 2 is a schematic process diagram of a method for water desalination and purification based on forward osmosis according to the present invention.
Figure 3:
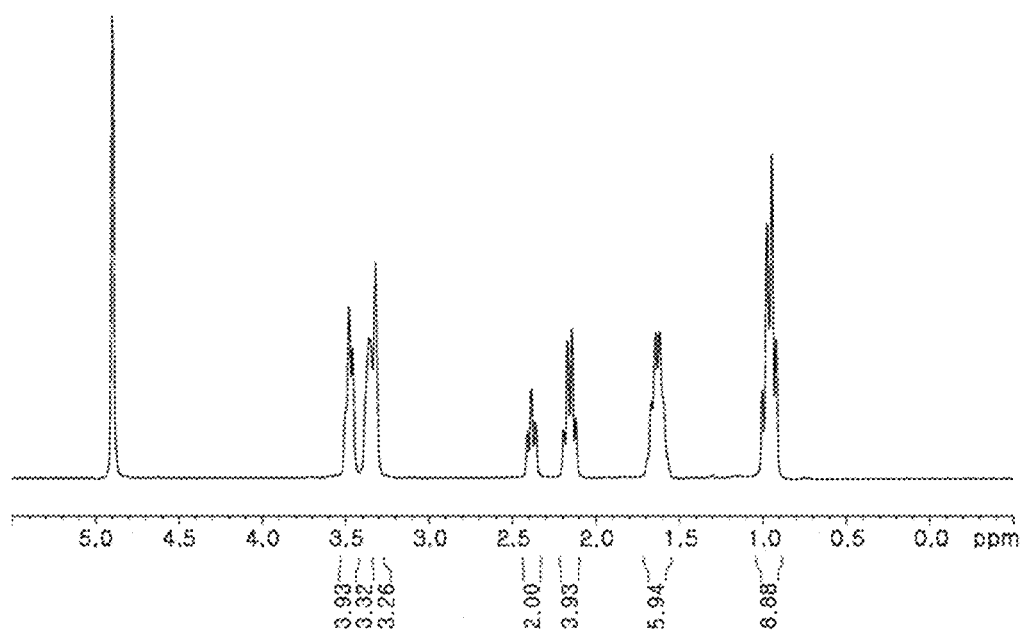
FIGS. 3 to 10 are $^1$H NMR spectra of nBu-DETA, Val-DEEA, iBu-DEEA, nBu-DAPMA, Val-DAPMA, nBu-DIPA, and PS-PEI, respectively, which were measured on a 300 MHz Bruker spectrometer.
Figure 4:
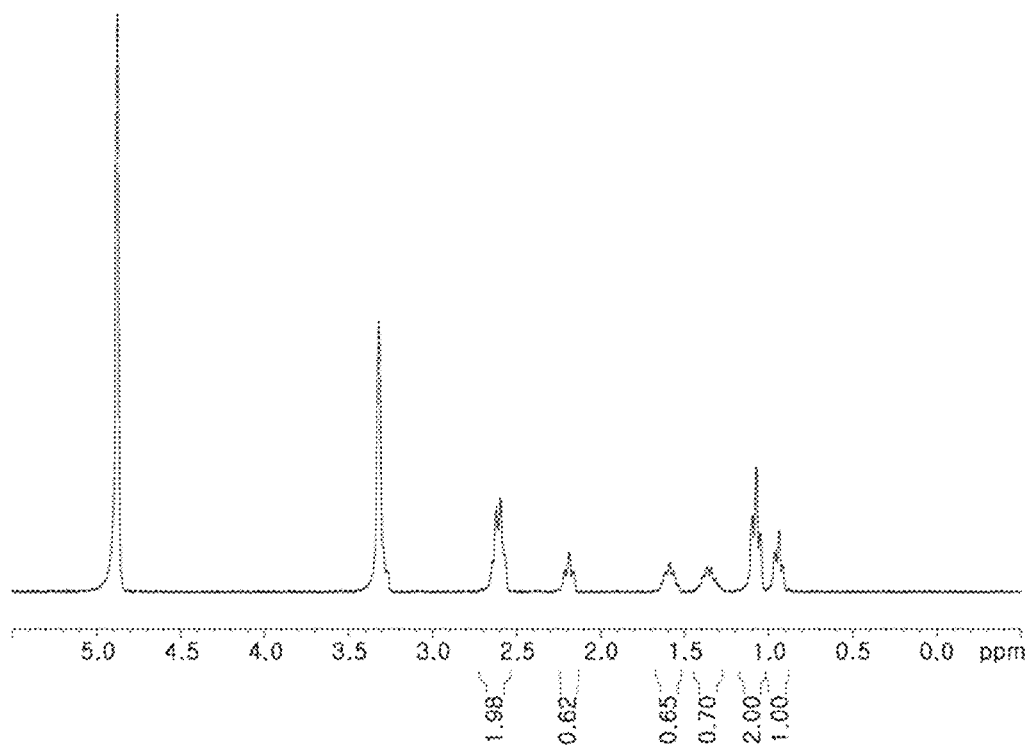
Figure 5:
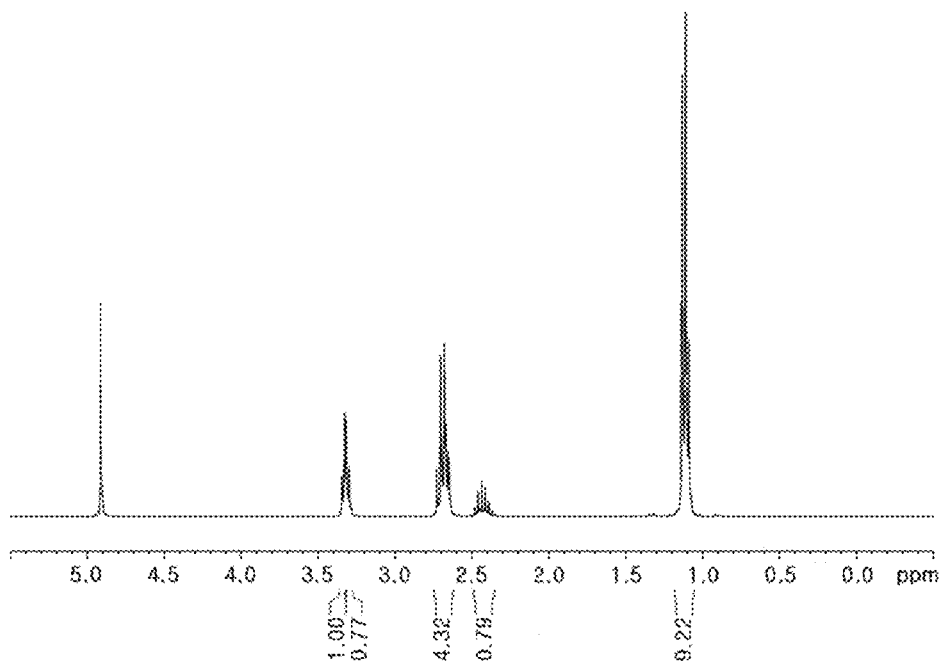
Figure 6:
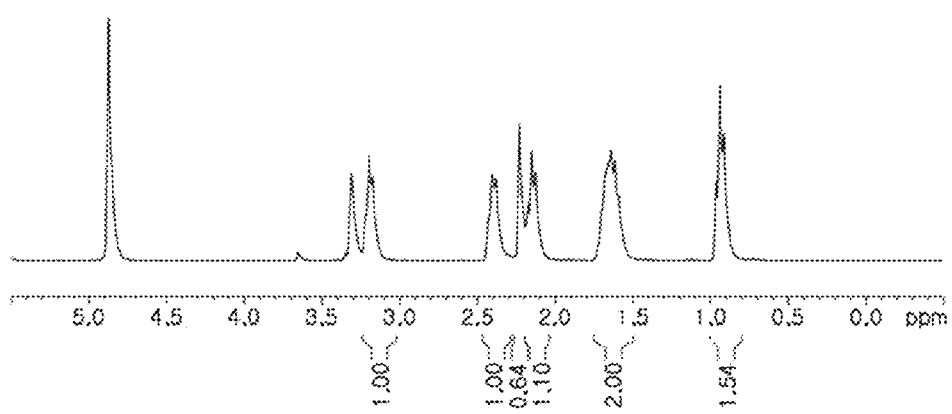
Figure 7:
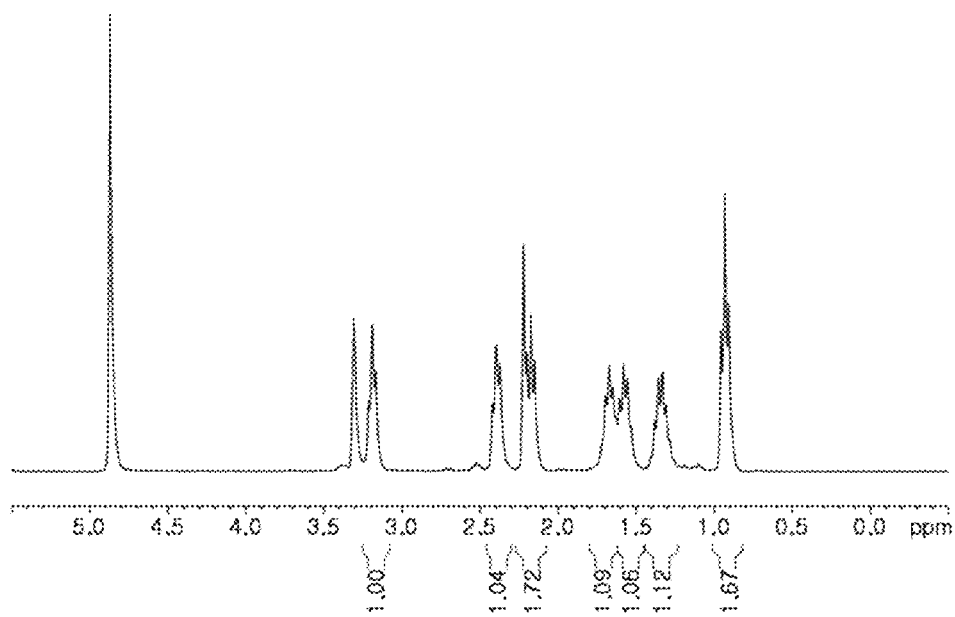
Figure 8:
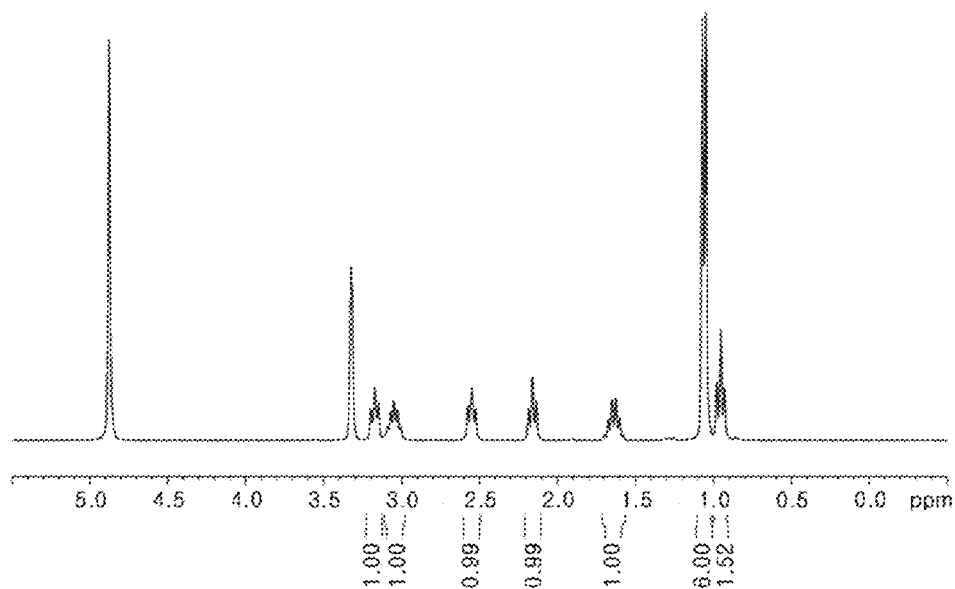

The present invention provides a method for water desalination and purification using a thermo-responsive draw solute for forward osmosis. FIG. 2 shows a schematic process diagram of the method for water desalination and purification according to the present invention. Referring to FIG. 2, first, 1) unpurified water is brought into contact with a draw solution including the thermo-responsive draw solute at a higher concentration than the unpurified water through a semi-permeable membrane (step ① of FIG. 2). Then, 2) clean water is allowed to flow from the unpurified water into the draw solution through the semi-permeable membrane by forward osmosis (step ② of FIG. 2). After the clean water has been moved to some extent, the contact between the draw solution and the unpurified water is blocked and 3) the temperature of the draw solution is raised to or above the critical solution temperature of the thermo-responsive draw solute to cause a phase transition of the thermo-responsive draw solute from the draw solution (step ③ of FIG. 2). Finally, 4) the clean water is separated from the draw solution, in which the phase transition of the draw solute has occurred, by general osmosis (step □ of FIG. 2).

The unpurified water, the draw solution, and available water (e.g., clean water or physiological saline) for the separation of clean water from the draw solution are in serial contact with each other, as shown in FIG. 2. In steps ① and ②, the unpurified water is brought into contact with the draw solution but the draw solution is blocked from contact with the available water. In steps 3) and 4), the unpurified water is blocked from contact with the draw solution and the draw solution is brought into contact with the available water. Since the osmotic pressure of the draw solution is greatly lowered after the phase transition of the thermo-responsive draw solute for forward osmosis, the clean water can be separated with low energy even by general reverse osmosis. In addition, even when physiological saline having the same salt concentration as the body fluid and brine having a lower salt concentration than the body fluid are used, water can be obtained from the draw solution by general osmosis.

The water desalination and purification method is based on forward osmosis using the draw solute having lower critical solution temperature characteristics. The thermo-responsive draw solute for forward osmosis may have a molar mass of 50 to 3000 g/mol. As described above, the thermo-responsive draw solute may undergo a phase transition at a reference temperature of 0° C. to 70° C. The draw solute for forward osmosis may be selected from the group consisting of:

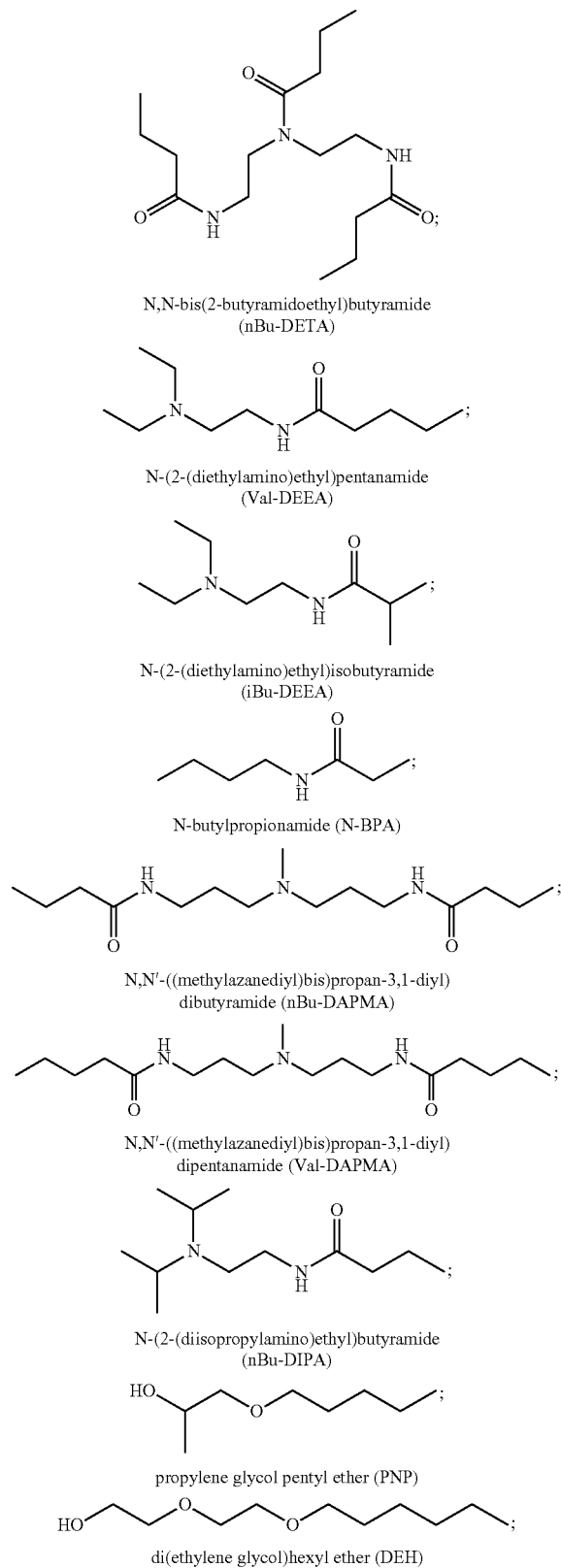

N,N-bis(2-butyramidoethyl)butyramide (nBu-DETA)

N-(2-(diethylamino)ethyl)pentanamide (Val-DEEA)

N-(2-(diethylamino)ethyl)isobutyramide (iBu-DEEA)

N-butylpropionamide (N-BPA)

N,N'-((methylazanediyl)bis)propan-3,1-diyl) dibutyramide (nBu-DAPMA)

N,N'-((methylazanediyl)bis)propan-3,1-diyl) dipentanamide (Val-DAPMA)

N-(2-(diisopropylamino)ethyl)butyramide (nBu-DIPA)

propylene glycol pentyl ether (PNP)

di(ethylene glycol)hexyl ether (DEH)

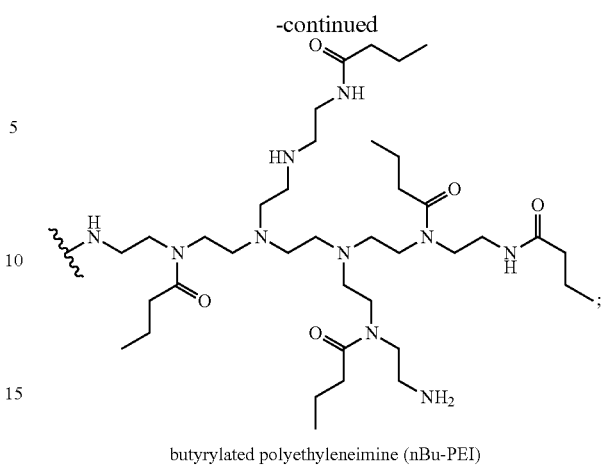

butyrylated polyethyleneimine (nBu-PEI)

and mixtures thereof.

The semi-permeable membrane arranged at the interface between the unpurified water and the draw solution and the semi-permeable membrane arranged at the interface between the draw solution and the available water may be those that are used in known water desalination or purification methods based on osmosis. Examples of suitable materials for the semi-permeable membranes include, but are not limited to, cellulose acetate and polyether sulfone.

Substances included in the unpurified water treated by the method of the present invention are not limited so long as they can be filtered by the semi-permeable membrane. Examples of such substances include ions, colloids, microbes, water soluble molecules, insoluble organic molecules, and mixtures thereof. The kind of the unpurified water is not particularly limited and may be, for example, seawater, river water or industrial wastewater. Particularly, considering the fact that the osmotic pressure of seawater is as very high as about 27 atm and ionic solutes such as sodium chloride accounting for the largest portion of seawater salinity have small particle sizes, the semi-permeable membrane should be dense. Accordingly, general forward osmosis systems capable of seawater desalination can purify almost all water species.

Alternatively, the water desalination and purification method of the present invention shown in FIG. 2 may be based on forward osmosis using the draw solute having upper critical solution temperature characteristics. In a further embodiment of the second aspect of the present invention, the method for water desalination and purification using the thermo-responsive draw solute for forward osmosis includes:

a method for water desalination and purification using a thermo-responsive draw solute for forward osmosis, the method including: 1) bringing unpurified water into contact with a draw solution including the thermo-responsive draw solute at a higher concentration than the unpurified water through a semi-permeable membrane; 2) allowing clean water to flow from the unpurified water into the draw solution through the semi-permeable membrane by forward osmosis; 3) raising the temperature of the draw solution to or below the critical solution temperature of the thermo-responsive draw solute to cause a phase transition of the thermo-responsive draw solute from the draw solution; and 4) separating the clean water from the draw solution.

The water desalination and purification method is based on forward osmosis using the draw solute having upper critical solution temperature characteristics. The thermo-responsive draw solute for forward osmosis may have a molar mass of 50 to 3000 g/mol. As described above, the thermo-responsive draw solute may undergo a phase transition at a reference temperature of 0° C. to 70° C. The draw solute for forward osmosis may be selected from the group consisting of:

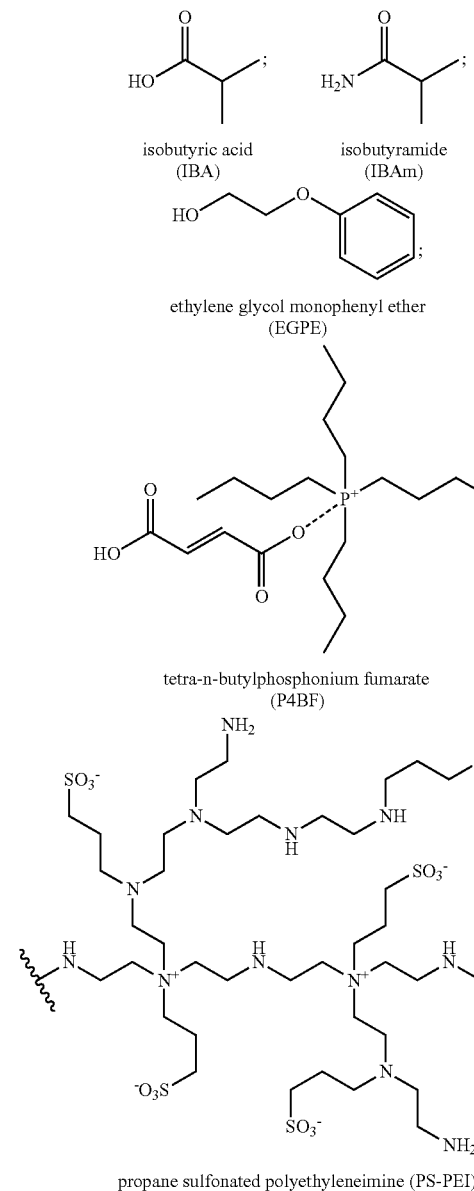

and
mixtures thereof.

The kind of the semi-permeable membrane used in the method of the present invention and the kind of the unpurified water treated by the method of the present invention are the same as those mentioned in the method using the draw solute having lower critical solution temperature characteristics.

MODE FOR INVENTION

The present invention will be explained in more detail with reference to the following examples. However, these examples are provided to assist in understanding the invention and are not intended to limit the scope of the invention.

EXAMPLES

Synthesis Example 1

Synthesis of Forward Osmosis Draw Solutes Having Lower Critical Solution Temperature Characteristics As suitable forward osmosis draw solutes having lower critical solution temperature characteristics, the following compounds were synthesized:

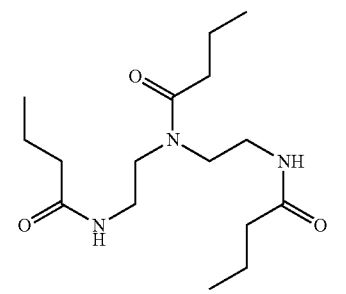

N,N-bis(2-butyramidoethyl)butyramide
(nBu-DETA)

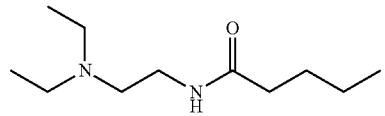

N-(2-(diethylamino)ethyl)pentanamide
(Val-DEEA)

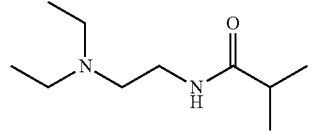

N-(2-(diethylamino)ethyl)isobutyramide
(iBu-DEEA)

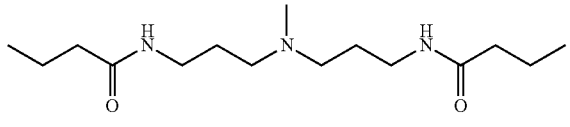

N,N'-((methylazanediyl)bis)propan-3,1-diyl)
dibutyramide (nBu-DAPMA)

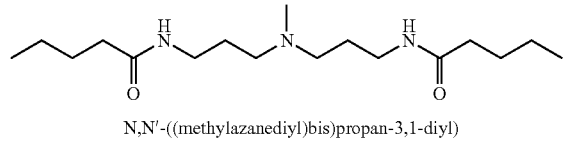

N,N'-((methylazanediyl)bis)propan-3,1-diyl)
dipentanamide (Val-DAPMA)

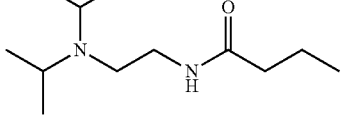

N-(2-(diisopropylamino)ethyl)butyramide
(nBu-DIPA)

The amine forms (Compounds 1 to 4) having no acyl groups of the compounds were prepared. 10 mL of each of the amine forms was dissolved in a solution of 200 mL of methanol and 200 mL of a 1 M sodium bicarbonate solution in a round-bottom flask. The temperature of the resulting solution was adjusted to 0° C. The acyl anhydride or acyl chloride (Compound a, b or c) having the corresponding acyl group was slowly added. 1.5 equivalents of the acyl anhydride or acyl chloride was used per equivalent of the primary and tertiary amino groups of the amine. The mixture was stirred at 0° C. for 1 h and at room temperature for additional 16-18 h.

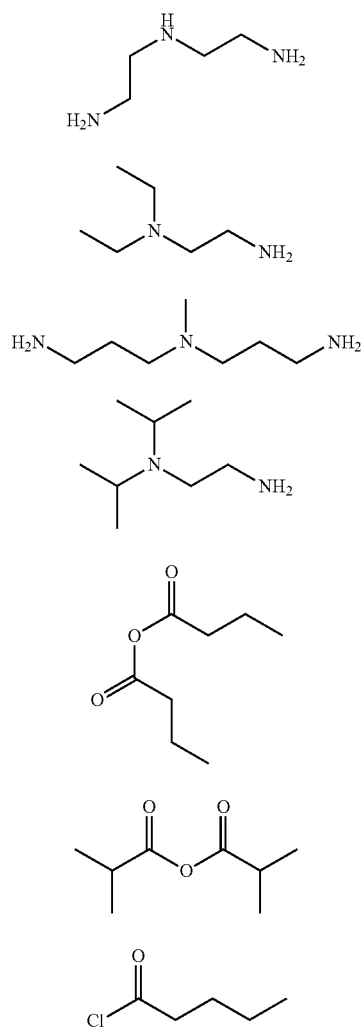

Compound 1
Compound 2
Compound 3
Compound 4
Compound a
Compound b
Compound c

Compound 1 + Compound a = nBu-DETA
Compound 2 + Compound b = iBu-DEEA
Compound 2 + Compound c = Val-DEEA
Compound 3 + Compound a = nBu-DAPMA
Compound 3 + Compound c = Val-DAPMA
Compound 4 + Compound a = nBu-DIPA After completion of the reaction, the reaction mixture was extracted about 2-4 times with dichloromethane, followed by drying to obtain the final product. $^1$H NMR spectra of nBu-DETA, Val-DEEA, iBu-DEER, nBu-DAPMA, Val-DAPMA, and nBu-DIPA measured on a 300 MHz Bruker spectrometer are shown in FIGS. 3 to 8, respectively.

As another forward osmosis draw solute having lower critical solution temperature characteristics, the following compound was synthesized:

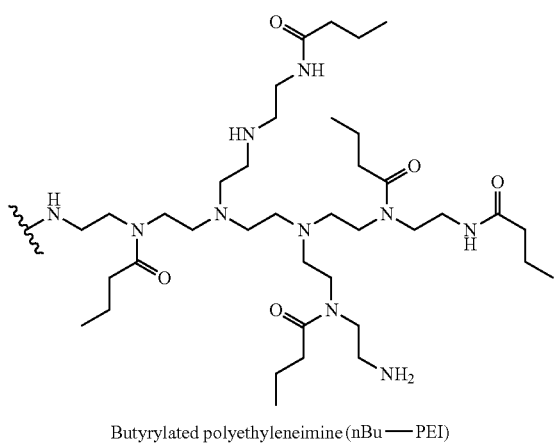

Butyrylated polyethyleneimine (nBu—PEI)

The compound was prepared by acylating polyethyleneimine (molecular weight=800 g/mol) with nbutyric anhydride having nbutyryl groups. It was found that 87% of the reactive primary and secondary amino groups of the polyethyleneimine were acylated (butyrylated) and the product had a molecular weight of 1650 g/mol.

Figure 9:
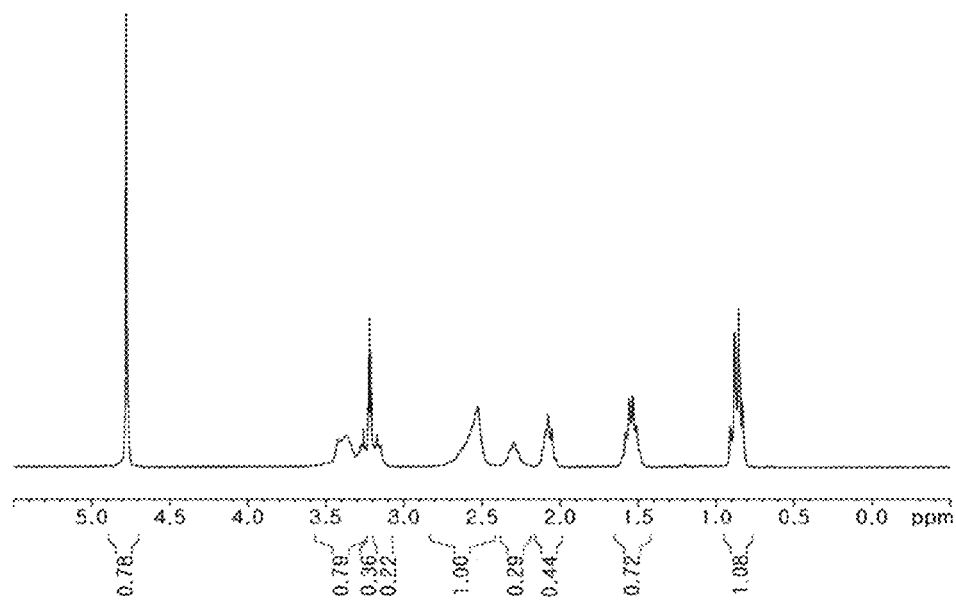

Specifically, 40 g of polyethyleneimine (molecular weight=800 g/mol) was dissolved in a solution of 400 ml of methanol and 400 mL of a 1 M sodium bicarbonate solution in a round-bottom flask. The temperature of the resulting solution was adjusted to 0° C., and then 103 mL of nbutyric anhydride was slowly added. The mixture was stirred at 0° C. for 1 h and at room temperature for additional 16-18 h. After completion of the reaction, the reaction mixture was extracted about 2-4 times with dichloromethane, followed by drying. The extract was dissolved in water and freeze-dried, yielding nBu-PEI as a yellow viscous liquid. FIG. 9 shows a $^1$H NMR spectrum of nBu-PEI measured on a 300 MHz Bruker spectrometer.

In addition to the synthesized forward osmosis draw solutes having lower critical solution temperature characteristics, the following commercially available forward osmosis draw solutes having lower critical solution temperature characteristics were purchased from Sigma-Aldrich:

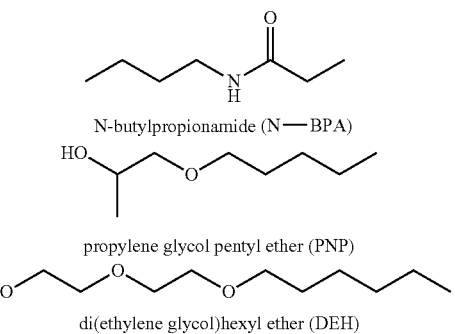

N-butylpropionamide (N—BPA)

propylene glycol pentyl ether (PNP)

di(ethylene glycol)hexyl ether (DEH)

Synthesis Example 2

Synthesis of Forward Osmosis Draw Solute Having Upper Critical Solution Temperature Characteristics As a suitable forward osmosis draw solute having upper critical solution temperature characteristics, the following compound was synthesized:

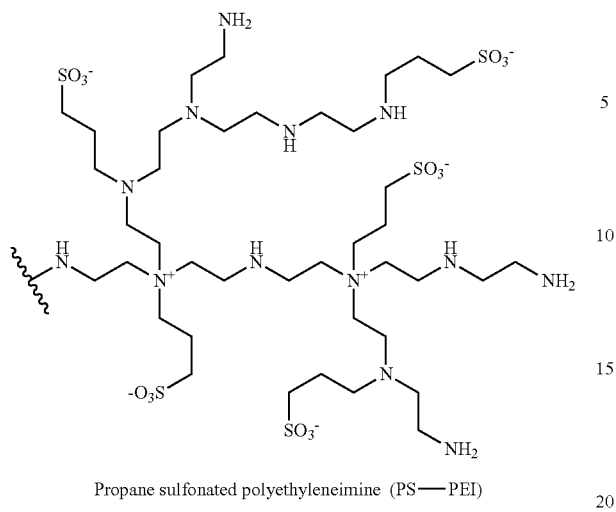

Propane sulfonated polyethyleneimine (PS—PEI)

In the compound, 60% of the reactive primary, secondary and tertiary amine groups of polyethyleneimine were sulfonated. The compound was found to have a molecular weight of 2162 g/mol. Specifically, the compound was prepared by the following procedure.

12 mL of 1,3-propanesultone was dissolved in 20 mL of methanol in a 70 mL vial. The vial was placed in a stirrer and the solution was stirred with a magnetic bar at 40° C. Subsequently, a solution of 6 g of polyethyleneimine (molecular weight=800 g/mol) in 10 mL of methanol was slowly added to the vial. The resulting mixture was stirred for about 24 h.

As the reaction proceeded, the product was settled down at the bottom of the vial and turned into a hard solid form because of its substantial insolubility in methanol. The hard solid was dissolved in 5 mL of a 2 M sodium hydroxide solution. The resulting solution was transferred to a 50 mL Falcon tube and 35 mL of methanol was added thereto to obtain a precipitate. Subsequently, the precipitate was completely settled using a centrifuge and the supernatant was discarded. This procedure was repeated 1-2 times.

The precipitate was dissolved in a small amount of water to remove sodium hydroxide included therein. Methanol was added to the aqueous solution. The precipitate was completely settled using a centrifuge in the same manner as above. This procedure was repeated 2-3 times.

Figure 10:
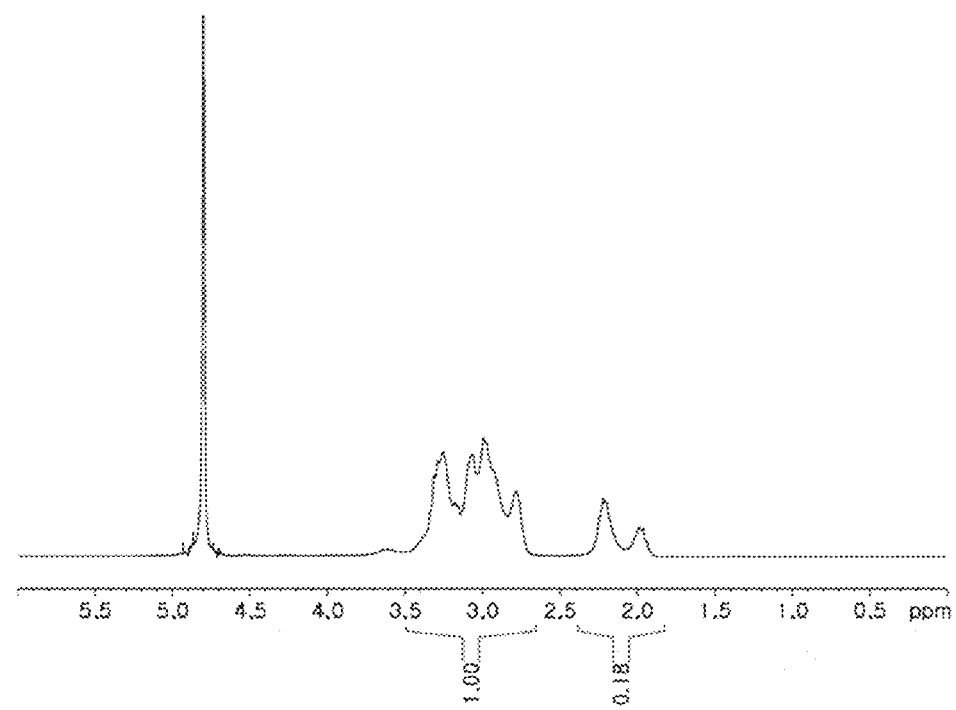

Subsequently, the precipitate was dissolved in a small amount of water. The solution was transferred to a round-bottom flask. The methanol was evaporated off using a rotary evaporator under vacuum. The product was dissolved in a small amount of water. The solution was divided into Falcon tubes, frozen with liquid nitrogen, and dried using a freeze dryer to obtain the final product. FIG. 10 shows a $^1H$ NMR spectrum of PS-PEI measured on a 300 MHz Bruker spectrometer.

In addition to the synthesized forward osmosis draw solute having upper critical solution temperature characteristics, the following commercially available forward osmosis draw solutes having upper critical solution temperature characteristics were purchased from Sigma-Aldrich:

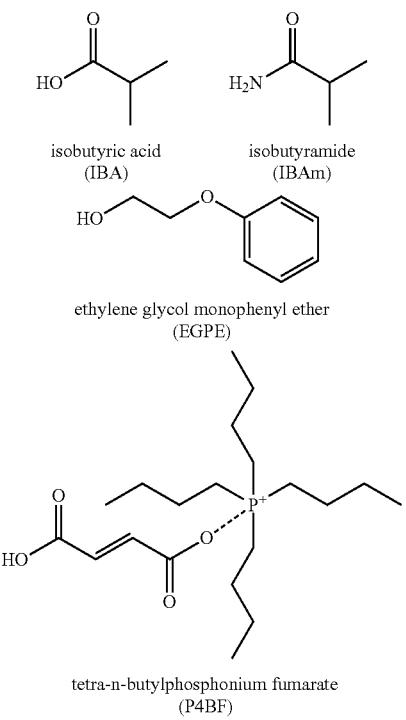

isobutyric acid (IBA)

isobutyramide (IBAm)

ethylene glycol monophenyl ether (EGPE)

tetra-n-butylphosphonium fumarate (P4BF)

EXPERIMENTAL EXAMPLES

Water Desalination and Purification Experiments Based on Forward Osmosis

Experimental Example 1

Measurement System

Figure 11:
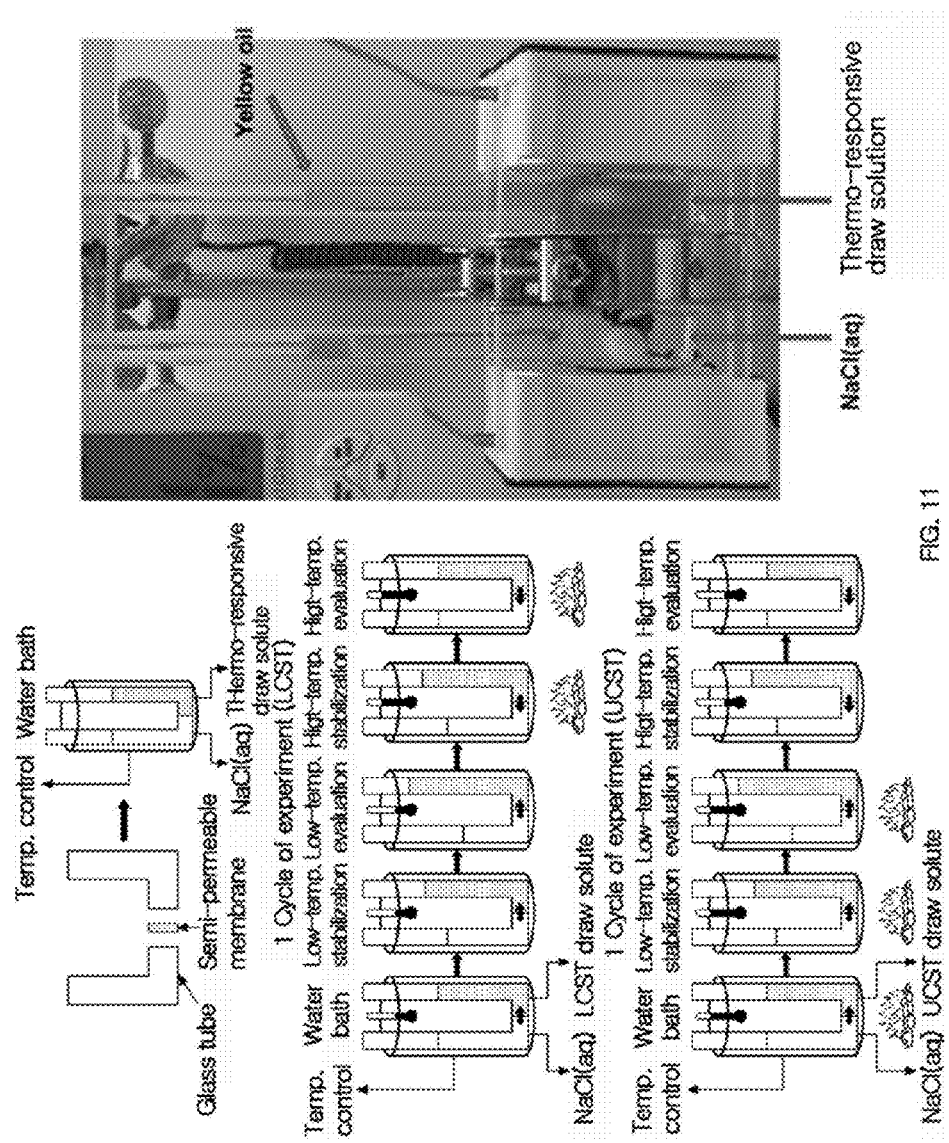
FIG. 11 shows a schematic design of a system for carrying out a water desalination and purification method based on forward osmosis according to the present invention, experimental processes using LCST and UCST draw solutes in the system, and an actual photograph of the system.
Figure 12:
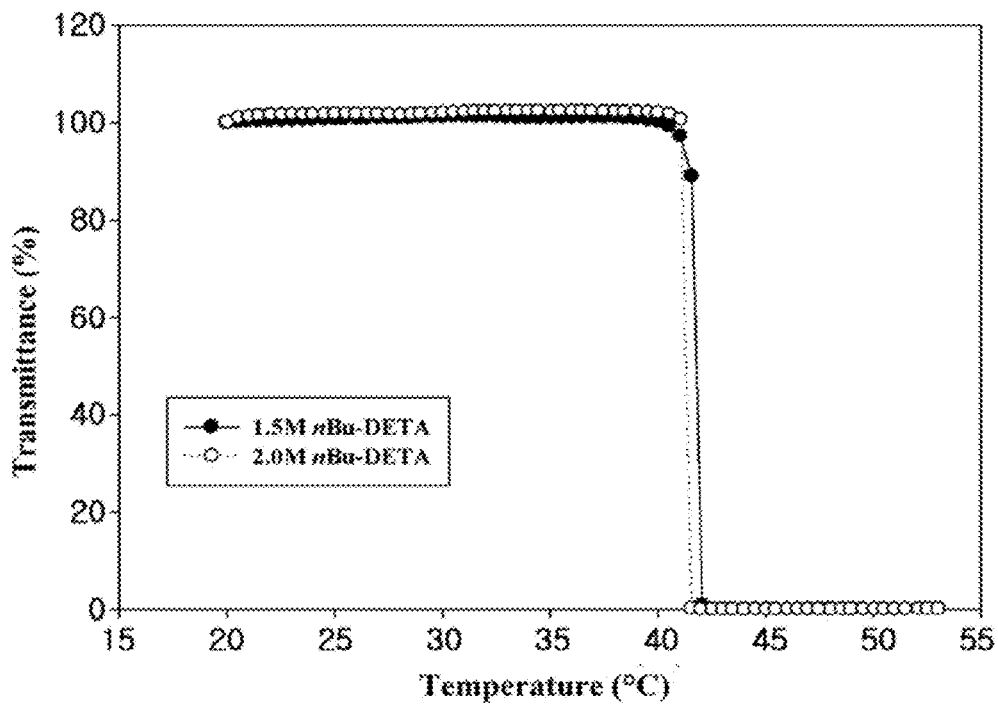
FIGS. 12 to 20 are graphs showing changes in the transmittance of nBu-DETA (FIG. 12), Val-DEEA and iBu-DEEA (FIG. 13), nBu-DAPMA and Val-DAPMA (FIG. 14), N-BPA and nBu-DIPA (FIG. 15), PNP and DEH (FIG. 16), nBu-PEI (FIG. 17), IBA and IBAm (FIG. 18), P4BF and EGPE (FIG. 19), and PS-PEI (FIG. 20) according to temperature variation.
Figure 13:
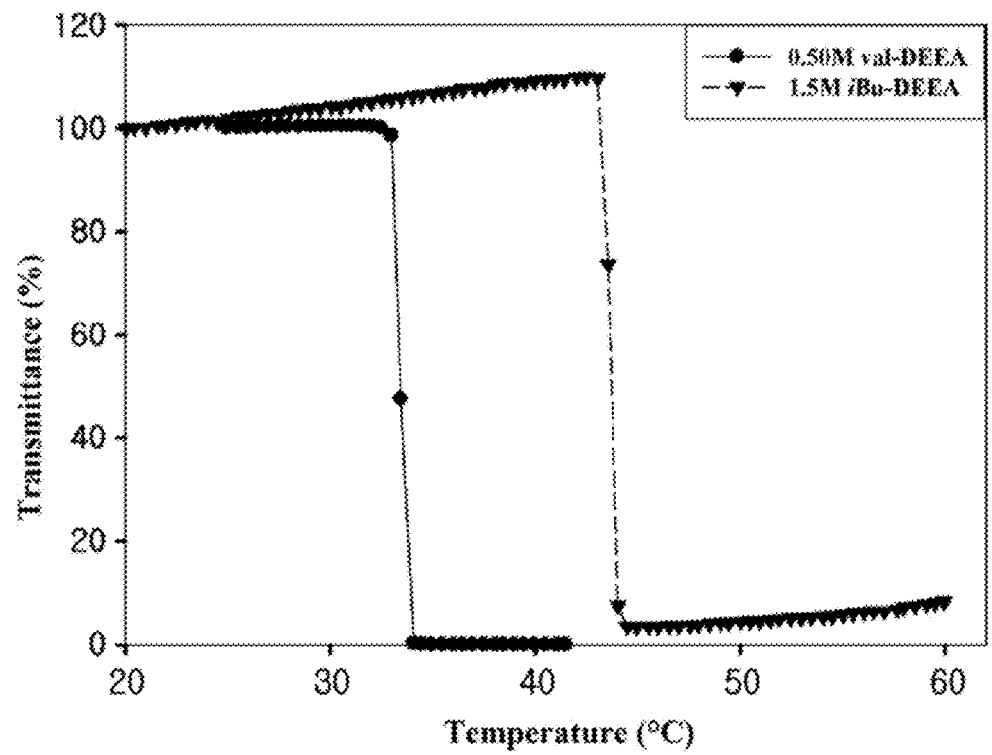
Figure 14:
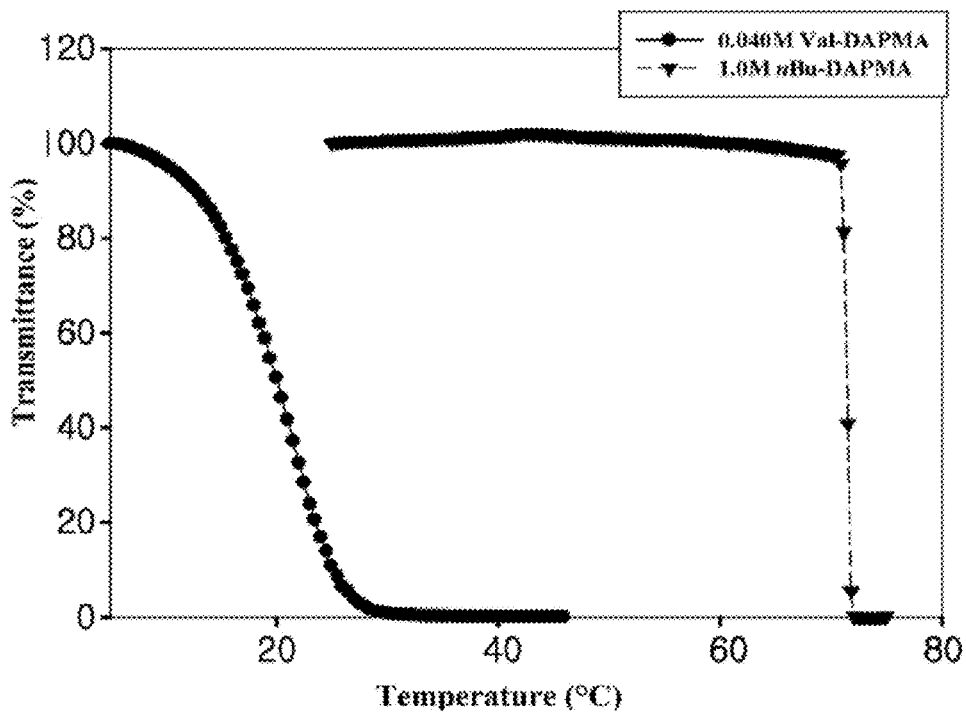
Figure 15:
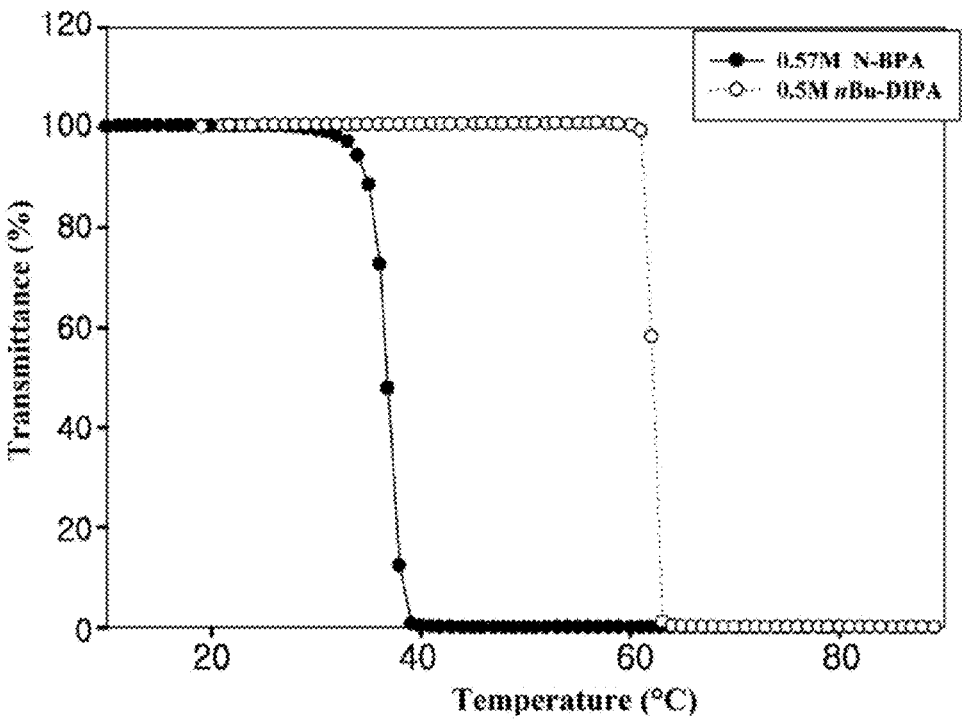
Figure 16:
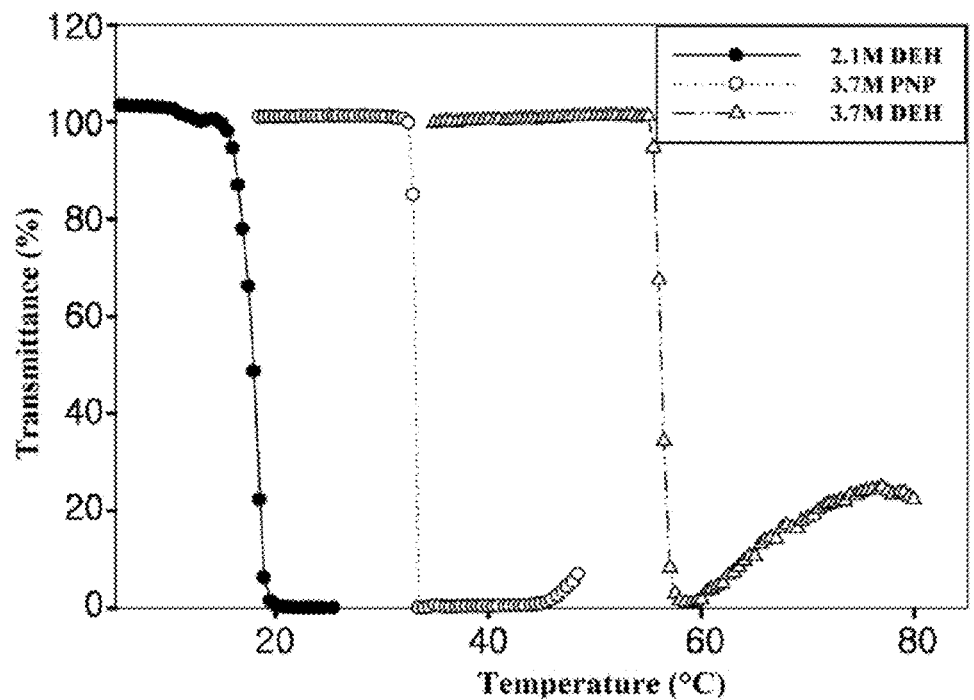
Figure 17:
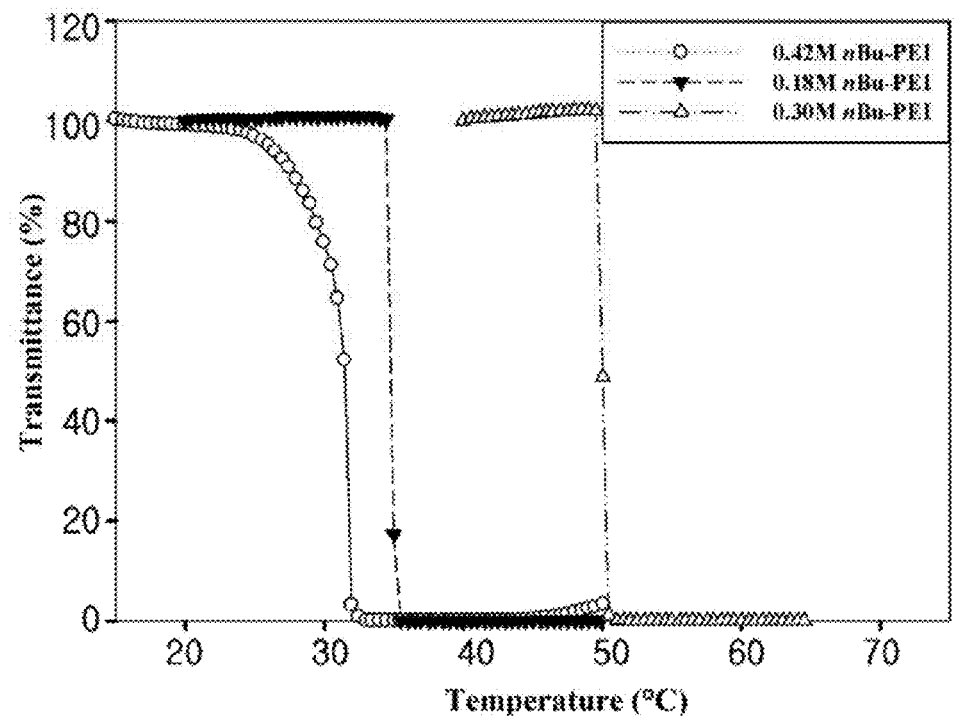

FIG. 11 shows a schematic design of a system for carrying out the water desalination and purification method based on forward osmosis according to the present invention, experimental processes using LCST and UCST draw solutes in the system, and an actual photograph of the system. Referring to FIG. 11, the system has a structure in which glass tubes are arranged to face each other through a semi-permeable membrane. Unpurified water is arranged in one of the glass tubes and a draw solution is arranged in the other glass tube. After the glass tubes are placed in a temperature-controllable water bath, water desalination and purification experiments are conducted. Specifically, the experiments using LCST draw solutes are carried out in the order of low temperature (homogeneous phase) and high temperature (phase transition). The experiments using UCST draw solutes are carried out in the order of high temperature (homogeneous phase) and low temperature (phase transition). As the semi-permeable membrane, a cellulose acetate semi-permeable membrane is used. Specifically, the semi-permeable membrane includes a support layer composed of a polyester fiber coated with polyethylene and a dense layer composed of a cellulose triacetate fiber. The semi-permeable membrane is characterized by the ability to remove 95% or more of salts and low-molecular-weight materials.

Experimental Example 2

Measurement of Transmittances According to Temperature Variation

LCST and UCST characteristics of the draw solutes mentioned in Synthesis Examples 1-2 were observed using the measurement system. For this observation, the transmittances of aqueous solutions of the draw solutes were measured using a UV/IR spectrometer.

Specifically, FIGS. 12 to 20 are graphs showing changes in the transmittance of nBu-DETA (FIG. 12), Val-DEEA and iBu-DEEA (FIG. 13), nBu-DAPMA and Val-DAPMA (FIG. 14), N-BPA and nBu-DIPA (FIG. 15), PNP and DEH (FIG. 16), nBu-PEI (FIG. 17), IBA and IBAm (FIG. 18), P4BF and EGPE (FIG. 19), and PS-PEI (FIG. 20) according to temperature variation.

Referring to FIGS. 12 to 17, the LCST draw solutes nBu-DETA (FIG. 12), Val-DEEA and iBu-DEEA (FIG. 13), nBu-DAPMA and Val-DAPMA (FIG. 14), N-BPA and nBu-DIPA (FIG. 15), PNP and DEH (FIG. 16), and nBu-PEI (FIG. 17) had a transmittance of 100% at temperatures lower than the respective reference temperatures, indicating that the draw solutes were well-dissolved in water and the solutions were thus transparent. As the temperature increased above each reference temperature, the draw solute aggregated and became large, making the solution opaque. As a result, light was scattered, resulting in a reduction in transmittance (%).

Figure 18:
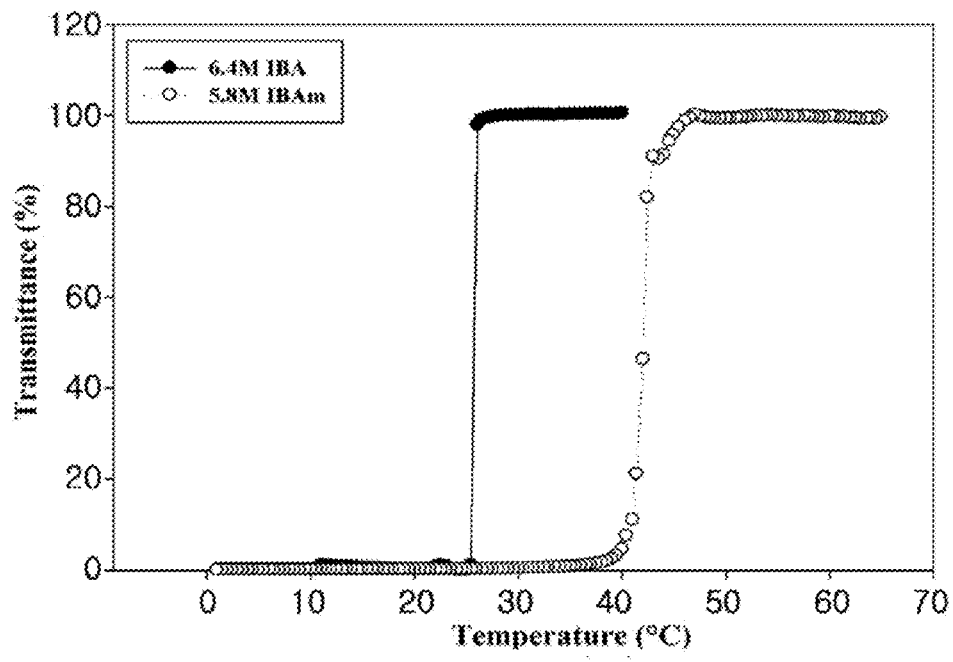
Figure 19:
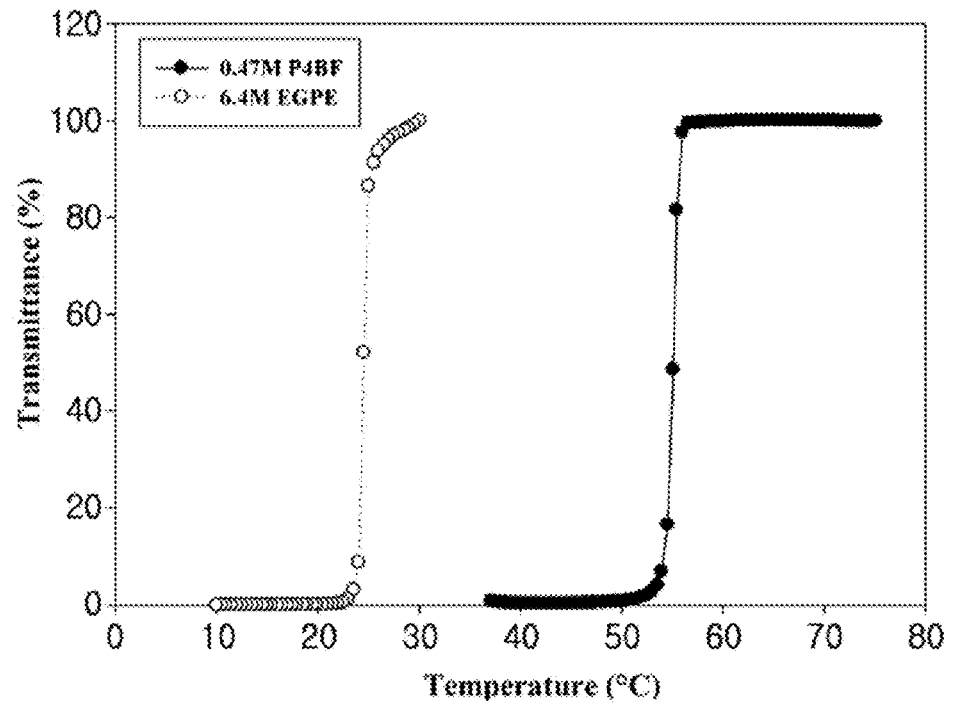
Figure 20:
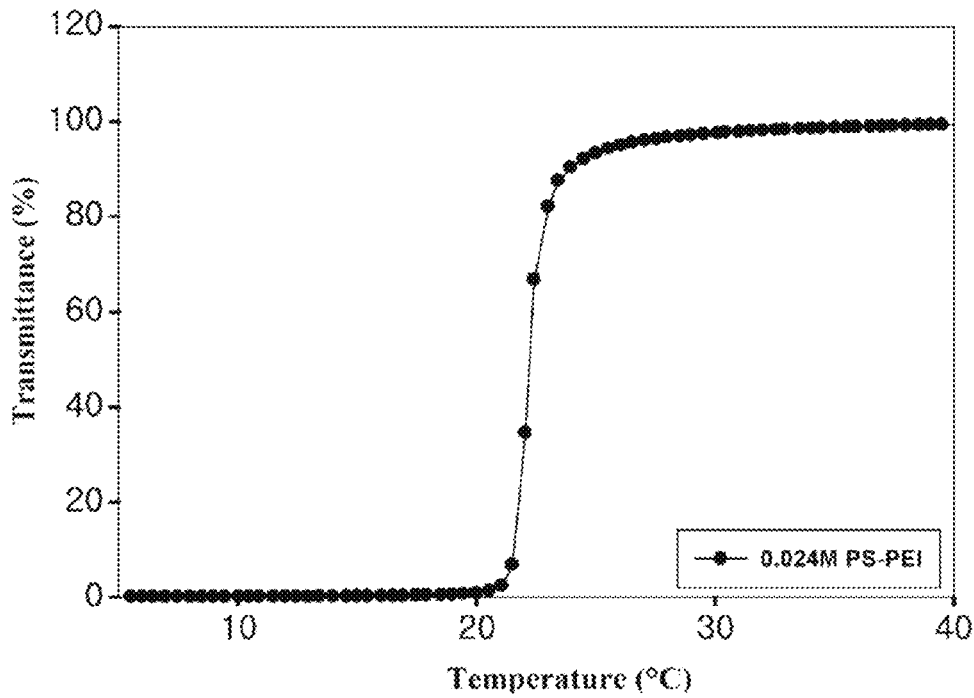

In contrast, referring to FIGS. 18 to 20, the UCST draw solutes IBA and IBAm (FIG. 18), P4BF and EGPE (FIG. 19), and PS-PEI (FIG. 20) had a transmittance of 100% at temperatures equal to or higher than the respective reference temperatures, indicating that the draw solutes were well-dissolved in water and the solutions were thus transparent. As the temperature decreased below each reference temperature, the draw solute aggregated and became large, making the solution opaque. As a result, light was scattered, resulting in a reduction in transmittance (%).

Experimental Example 3

Measurement of Flows and Fluxes of Water

Forward osmosis experiments were conducted at laboratory level using the thermo-responsive draw solutes synthesized above. The fluxes and directivities of water at low/high temperatures were confirmed with varying concentrations of brines and the draw solutions.

A stirrer was installed to maintain a uniform state of the solution in each glass tube and a thermostatic bath was installed for temperature control. After the temperature was maintained constant, the flux of water was measured. The amount of water flowing through the membrane was expressed in volume per unit area of the membrane and unit time (L/m$^2$h, LMH). The fluxes and directivities of water at low and high temperatures were measured at time points of each experiment. For better visual observation, a slight amount of dye was added to the system.

Experimental Example 3-1

Measurement of Flows and Fluxes of Water when nBu-DETA was Used

Flow and Fluxes of Water at Low Temperature

Figure 21:
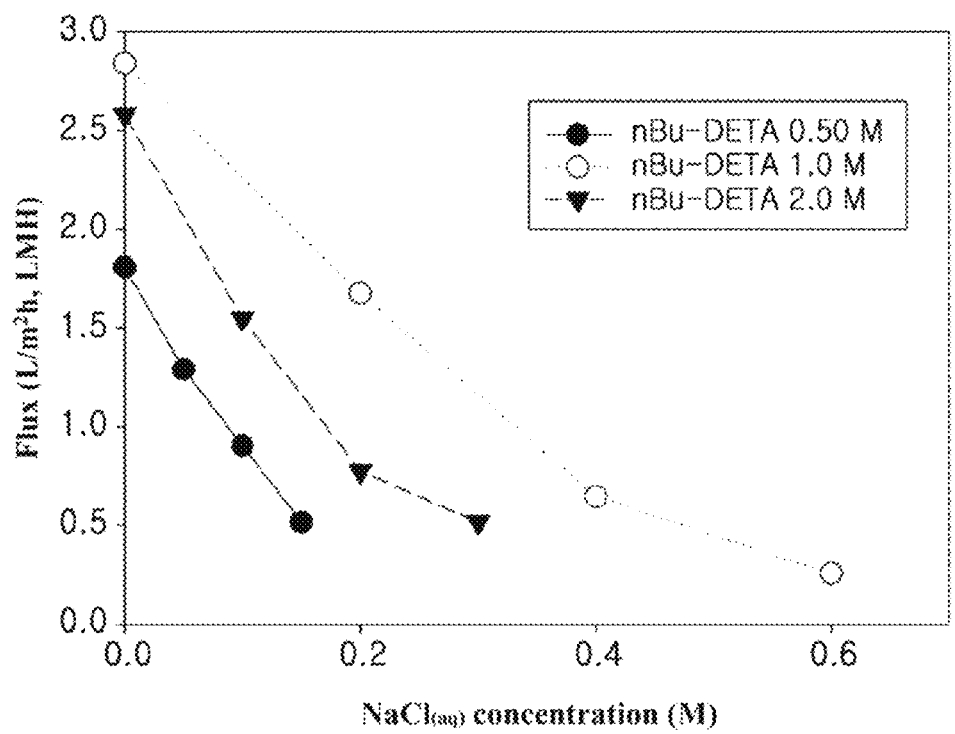
FIG. 21 is a graph showing changes in the flux of water at various NaCl concentrations of brines and various concentrations of draw solutions in an experiment for the measurement of the flow and fluxes of water at a low temperature when nBu-DETA was used.

The draw solute nBu-DETA was confirmed to draw clean water from various levels of brines. Table 1 and FIG. 21 summarize the fluxes of water at various NaCl concentrations of brines and various concentrations of draw solutions. Table 1 shows the fluxes (LMH) of water at 18 (±0.5)° C. (flow direction: NaCl→nBu-DETA).

Referring to Table 1 and FIG. 21, the flux of water was increased with increasing concentration of the nBu-DETA draw solution. Particularly, it was confirmed that the 2.0 M nBu-DETA solution could draw clean water from the 0.6 M NaCl solution, which corresponds to the level of seawater.

TABLE 1

|  | 0.5M nBu-DETA | 1.0M nBu-DETA | 2.0M nBu-DETA |
| --- | --- | --- | --- |
| 0.050M NaCl | 1.3 | — | — |
| 0.10M NaCl | 0.90 | 1.5 | — |
| 0.15M NaCl | 0.52 | — | — |
| 0.20M NaCl | — | 0.77 | 1.7 |
| 0.30M NaCl | — | 0.52 | — |
| 0.40M NaCl | — | — | 0.65 |
| 0.60M NaCl | — | — | 0.26 |

Flow and Fluxes of Water at High Temperature

Figure 22:
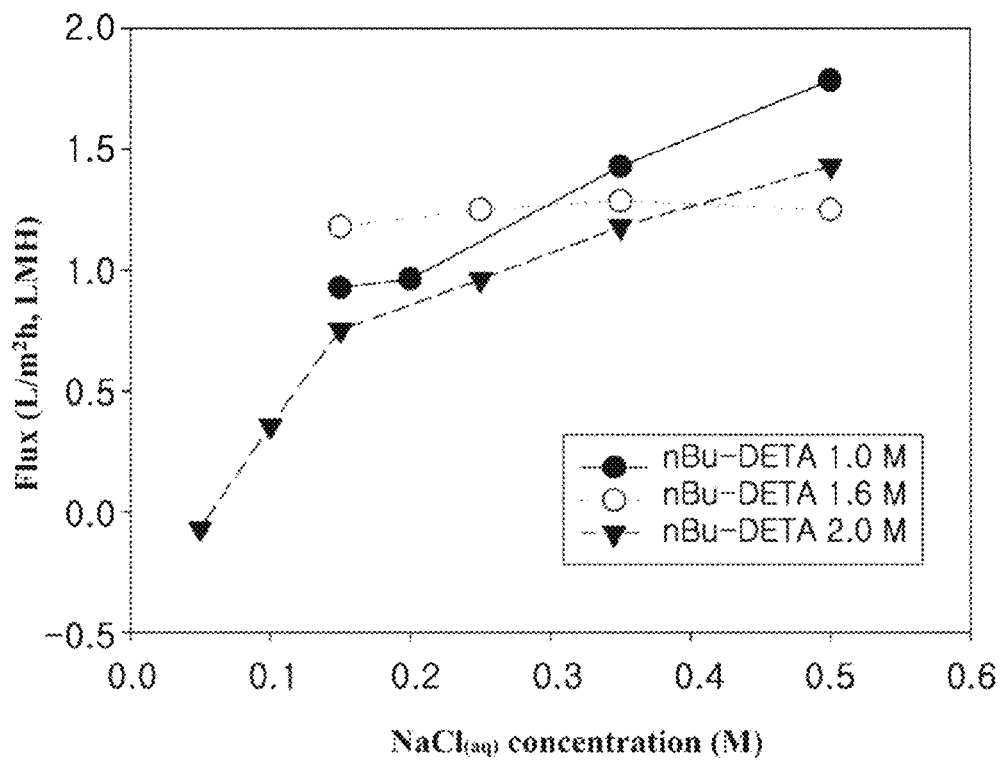
FIG. 22 is a graph showing changes in the flux of water at various NaCl concentrations of brines and various concentrations of draw solutions in an experiment for the measurement of the flow and fluxes of water at a high temperature when nBu-DETA was used.

It was confirmed that nBu-DETA synthesized in Synthesis Example 1 underwent a phase transition in draw solutions at a high temperature and could draw clean water from various levels of brines. Table 2 and FIG. 22 summarize the fluxes of water at various NaCl concentrations of brines and various concentrations of draw solutions. Table 2 shows the fluxes (LMH) of water at 70 (±0.5)° C. (flow direction: nBu-DETA→NaCl). Particularly, it was confirmed that the 0.15 M NaCl solution, which corresponds to the concentration of physiological saline, could draw clean water from the 2.0 M nBu-DETA solutions.

TABLE 2

|  | 1.0M nBu-DETA | 1.6M nBu-DETA | 2.0M nBu-DETA |
| --- | --- | --- | --- |
| 0.05M NaCl | — | — | −0.071 |
| 0.1M NaCl | — | — | 0.36 |
| 0.15M NaCl | 0.93 | 1.2 | 0.75 |
| 0.2M NaCl | 0.96 | — | — |
| 0.25M NaCl | — | 1.2 | 0.96 |
| 0.35M NaCl | 1.4 | 1.3 | 1.2 |
| 0.5M NaCl | 1.8 | 1.2 | 1.4 |

Experimental Example 3-2

Measurement of Flows and Fluxes of Water when DEH was Used

Flow and Fluxes of Water at Low Temperature 4.0 M solution of DEH, a commercially available draw solute, was confirmed to draw clean water from 0.6 M brine. Table 3 summarizes the flux of water from the 0.6 M brine. Table 3 shows the flux (LMH) of water at 18 (±0.5)° C. (flow direction: NaCl→DEH).

Referring to Table 3, the 4.0 M DEH was confirmed to draw clean water from the 0.6 M NaCl solution, which corresponds to the level of seawater.

TABLE 3

| NaCl (M) | Flux (LMH) |
| --- | --- |
| 0.60 | 0.29 |

Flow and Fluxes of Water at High Temperature

Figure 23:
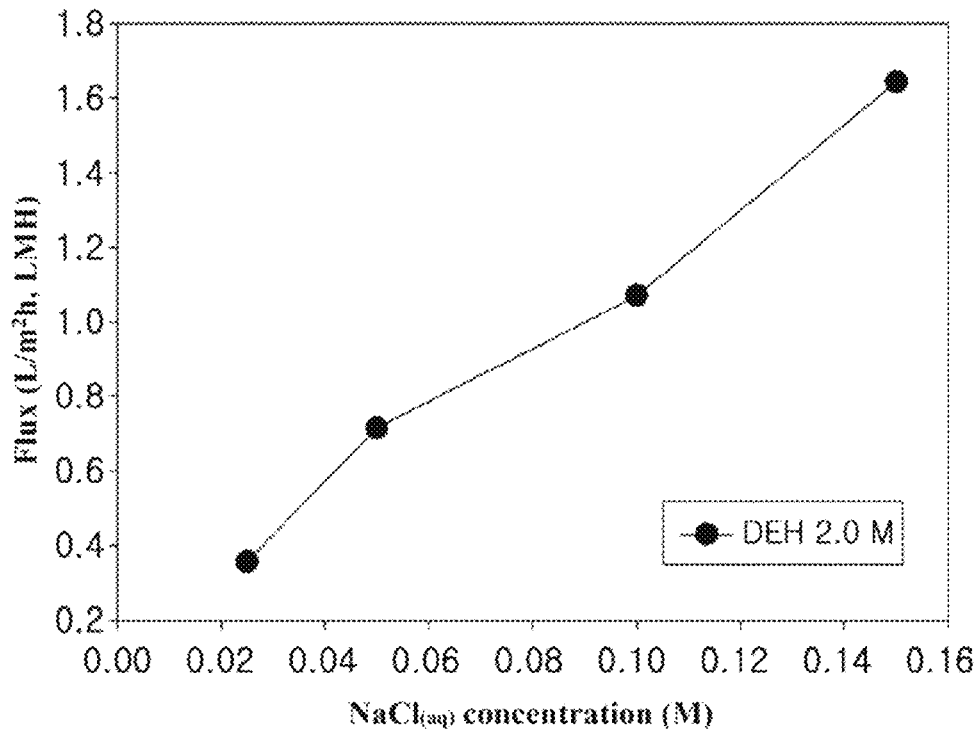
FIG. 23 is a graph showing changes in the flux of water at various NaCl concentrations of brines and various concentrations of a draw solution in an experiment for the measurement of the flow and fluxes of water at a high temperature when DEH was used.

It was confirmed that DEH underwent a phase transition in a 2 M draw solution at a high temperature and could draw clean water from various brines. Table 4 and FIG. 23 summarize the fluxes of water at various NaCl concentrations of brines. Table 4 shows the fluxes (LMH) of water at 40 (+0.5)° C. (flow direction: DEH→NaCl). Particularly, it was confirmed that the 0.15 M NaCl solution, which corresponds to the concentration of physiological saline, could draw clean water from the 2.0 M DEH solution.

TABLE 4

| NaCl (M) | Flux (LMH) |
|---|---|
| 0.025 | 1.6422 |
| 0.05 | 1.1 |
| 0.1 | 0.71 |
| 0.15 | 0.36 |

Experimental Example 3-3

Measurement of Flows and Fluxes of Water when nBu-PEI was Used

Flow and Fluxes of Water at Low Temperature

Figure 24:
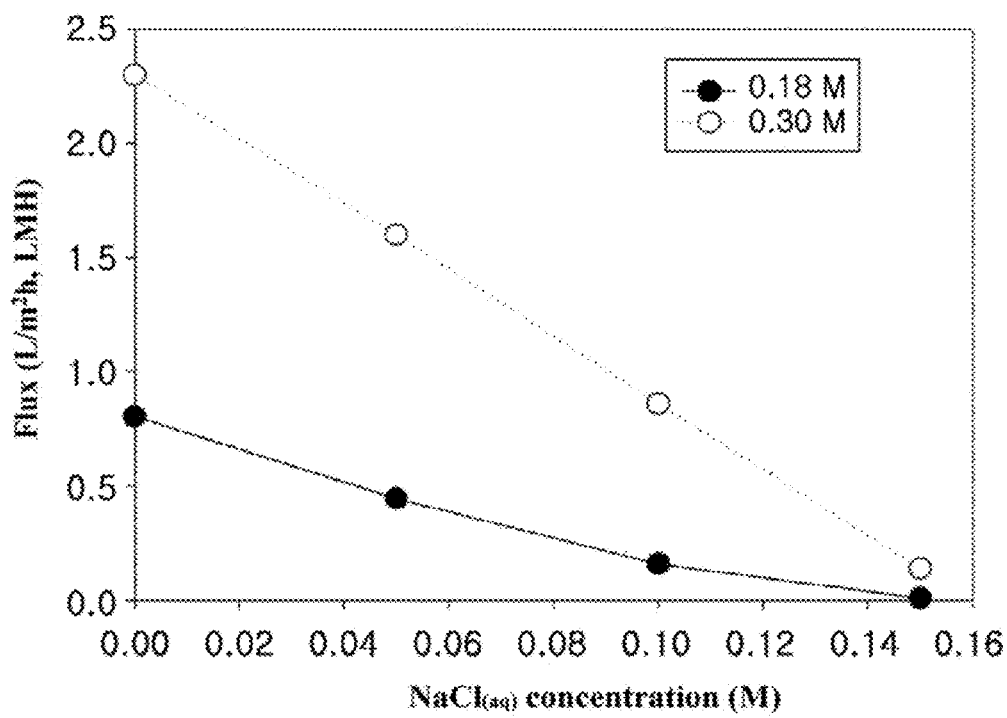
FIG. 24 is a graph showing changes in the flux of water at various NaCl concentrations of brines and various concentrations of draw solutions in an experiment for the measurement of the flow and fluxes of water at a low temperature when nBu-PEI was used.

The draw solute nBu-PEI was confirmed to draw clean water from various levels of brines. Table 5 and FIG. 24 summarize the fluxes of water at various NaCl concentrations of brines and various concentrations of draw solutions. Table 5 shows the fluxes (LMH) of water at 18 (±0.5)° C. (flow direction: NaCl→nBu-PEI). Referring to Table 5 and FIG. 24, the flux of water was increased with increasing concentration of the nBu-DETA draw solution.

TABLE 5

| | 0.18M nBu-PEI | 0.30M nBu-PEI |
|---|---|---|
| DW | 0.80 | 2.3 |
| 0.050M NaCl | 0.45 | 1.6 |
| 0.10M NaCl | 0.16 | 0.86 |
| 0.15M NaCl | 0.010 | 0.14 |

Flow and Fluxes of Water at High Temperature

Figure 25:
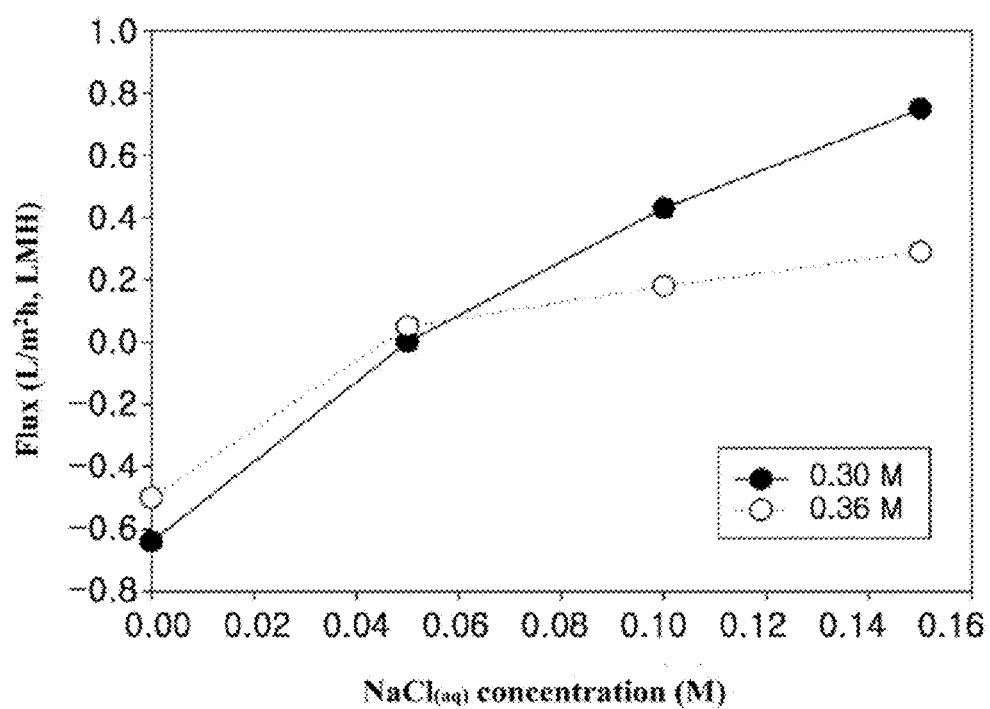
FIG. 25 is a graph showing changes in the flux of water at various NaCl concentrations of brines and various concentrations of draw solutions in an experiment for the measurement of the flow and fluxes of water at a high temperature when nBu-PEI was used.

It was confirmed that nBu-PEI synthesized in Synthesis Example 1 underwent a phase transition in draw solutions at a high temperature and could draw clean water from various levels of brines. Table 6 and FIG. 25 summarize the fluxes of water at various NaCl concentrations of brines and various concentrations of draw solutions. Table 6 shows the fluxes (LMH) of water at 55 (±0.5)° C. (flow direction: nBu-PEI→NaCl). Particularly, it was confirmed that the 0.15 M NaCl solution, which corresponds to the concentration of physiological saline, could draw clean water from the nBu-PEI solutions.

TABLE 6

| | 0.30M nBu-PEI | 0.36M nBu-PEI |
|---|---|---|
| DW | −0.64 | −0.50 |
| 0.050M NaCl | 0 | 0.050 |
| 0.10M NaCl | 0.43 | 0.18 |
| 0.15M NaCl | 0.75 | 0.29 |

Experimental Example 3-4

Measurement of Flows and Fluxes of Water when EGPE was Used

Flow and Flux of Water at High Temperature 6.4 M solution of EGPE, a commercially available draw solute, was confirmed to draw clean water from 0.3 M brine. The flux of water from NaCl to EGPE at 50° C. was 0.14 LMH.

Flow and Flux of Water at Low Temperature

It was confirmed that EGPE, a commercially available draw solute, underwent a phase transition in a 6.4 M draw solution at a low temperature and could draw clean water from 0.15 M brine. The flux of water from EGPE to NaCl at 5° C. was 0.036 LMH.

Experimental Example 3-5

Measurement of Flows and Fluxes of Water when PS-PEI was Used 10.1 g of propane sulfonated-polyethyleneimine was dissolved in distilled water to prepare 31 mL of a 0.15 M solution. The solution was acidified with a 2 M hydrochloric acid solution. The resulting solution had an upper critical solution temperature of 20-40° C. and a concentration of 0.60 M. An osmosis control experiment was conducted using the 0.60 M propane sulfonated-polyethyleneimine solution and 0.25 M NaCl. The experimental results showed that the flux of freshwater from the NaCl solution to the propane sulfonated-polyethyleneimine solution was 0.086 LMH at 60° C. where no phase transition occurred, whereas a concentration inversion was observed at 5° C. where a phase transition occurred. Therefore, the flux of freshwater from the propane sulfonated-polyethyleneimine solution to the NaCl solution at 5° C. was 0.086 LMH.

Tables 7 and 8 show the flows and fluxes of water at a high temperature (60° C.) and a low temperature (5° C.), respectively.

TABLE 7

| | 0.15M PS-PEI + 0.45M Cl− |
|---|---|
| 0.25M NaCl | 0.086 LMH |

TABLE 8

| | 0.15M PS-PEI + 0.45M Cl− |
|---|---|
| 0.25M NaCl | 0.086 LMH |

Experimental Example 4

Verification of Reproducibility of Forward Osmosis Experiments

Figure 26:
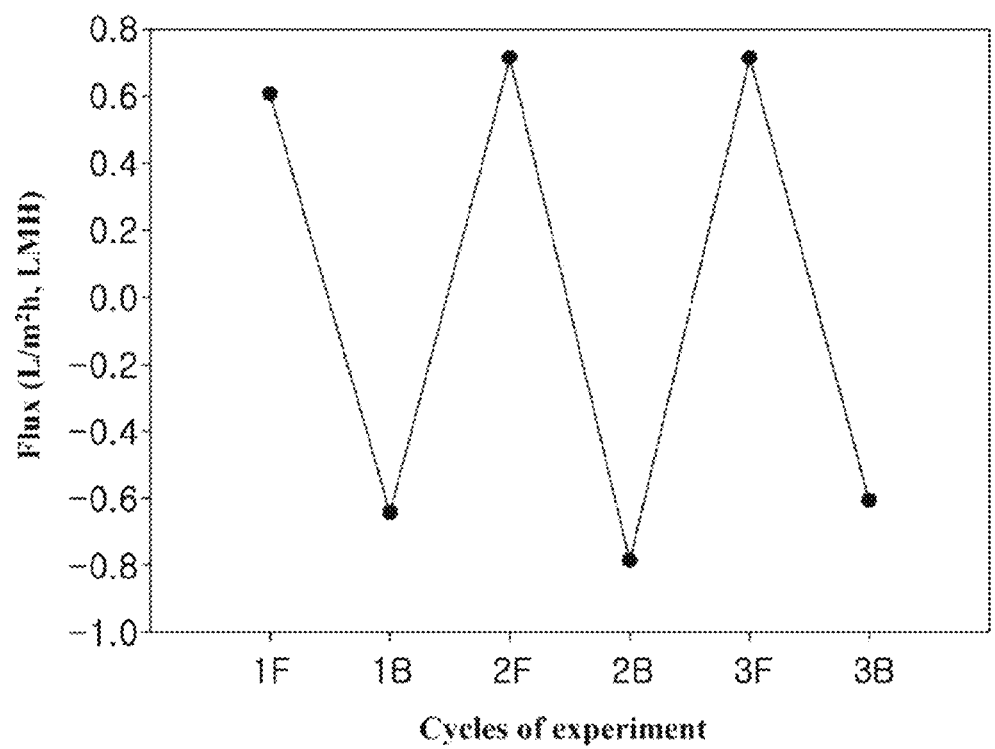
FIG. 26 is a graph showing changes in the flux of water during repeated experiments using nBu-DETA.

A draw solute for a forward osmosis process should be able to be continuously reused after the process. The fluxes of water at low and high temperatures were measured alternately three consecutive times using a UV/IR spectrometer to confirm whether the material had a constant phase transition temperature despite repeated phase transitions. FIG. 26 is a graph showing changes in the flux of water during repeated experiments using 2.0 M nBu-DETA. As can be seen from the graph, the fluxes of water were maintained substantially constant despite the three repeated cycles of forward osmosis. The results of FIG. 26 are shown in Table 9.

TABLE 9

| 18° C. | Flux (L/m$^2$h) | 70° C. | Flux (L/m$^2$h) |
|---|---|---|---|
| 1 Cycle | 0.61 | 1 Cycle | −0.64 |
| 2 Cycle | 0.71 | 2 Cycle | −0.79 |
| 3 Cycle | 0.71 | 3 Cycle | −0.61 |

(The positive values in Table 9 represent flow of water from brine to nBu-DETA solution)

In a conventional process using ammonium carbonate/ammonium hydroxide, recondensation is required to reuse recovered ammonia and carbon dioxide molecules. In contrast, in the three repeated cycles of forward osmosis using nBu-DETA as a draw solute, any special process for dissolution except stirring was not carried out but the solute having undergone a phase transition were dissolved when hot water was exchanged with cold water in the thermostatic bath. As a result, similar levels of fluxes were obtained, which can be seen from FIG. 26 and Table 9.

INDUSTRIAL APPLICABILITY

According to the present invention, seawater and various types of contaminated water can be effectively desalinated or purified. Therefore, the present invention can find application in various industrial fields, including water treatment.

The invention claimed is:
1. A method for water desalination and purification using a thermo-responsive draw solute for forward osmosis, the method comprising:
   1) bringing unpurified water into contact with a draw solution comprising the thermo-responsive draw solute at a higher concentration than the unpurified water through a semi-permeable membrane;
   2) allowing clean water to flow from the unpurified water into the draw solution through the semi-permeable membrane by forward osmosis;
   3) adjusting the temperature of the draw solution to or above the critical solution temperature of the thermo-responsive draw solute to cause a lower critical solution temperature (LCST) phase separation of the thermo-responsive draw solute from the draw solution; and
   4) separating the clean water from the thermo-responsive draw solution.
2. The method according to claim 1, wherein the thermo-responsive draw solute for forward osmosis has a molar mass of 50 to 3000 g/mol and undergoes a LCST phase transition at a temperature of 0° C. to 70° C.
3. The method according to claim 1, wherein the thermo-responsive draw solute for forward osmosis is selected from the group consisting of:

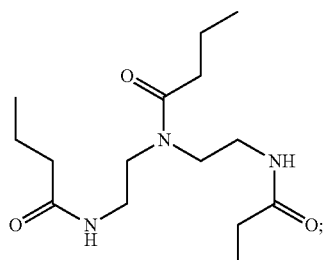

N,N-bis(2-butyramidoethyl)butyramide (nBu-DETA)

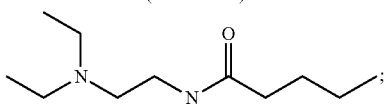

N-(2-(diethylamino)ethyl)pentanamide (Val-DEEA)

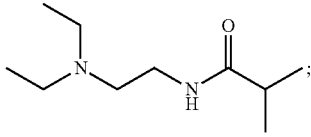

N-(2-(diethylamino)ethyl)isobutyramide (iBu-DEEA)

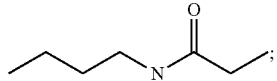

N-butylpropionamide (N-BPA)

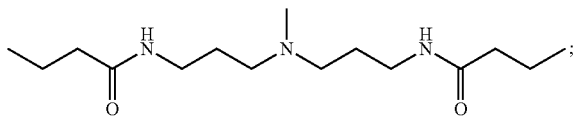

N,N'-((methylazanediyl)bis)propan-3,1-diyl) dibutyramide (nBu-DAPMA)

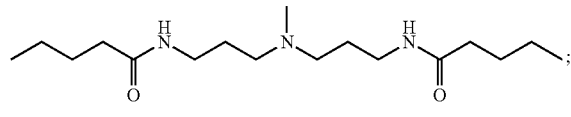

N,N'-((methylazanediyl)bis)propan-3,1-diyl) dipentanamide (Val-DAPMA)

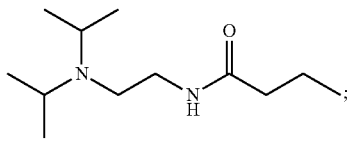

N-(2-(diisopropylamino)ethyl)butyramide (nBu-DIPA)

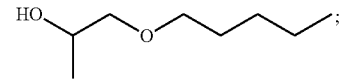

propylene glycol pentyl ether (PNP)

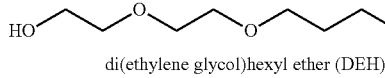

di(ethylene glycol)hexyl ether (DEH)

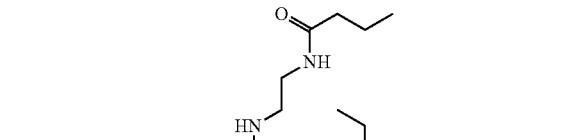

butyrylated polyethyleneimine (nBu-PEI)

and mixtures thereof.
4. The method according to claim 1, wherein the semi-permeable membrane is a cellulose acetate or polyether sulfone semi-permeable membrane.
5. The method according to claim 1, wherein the unpurified water is water comprising ions, colloids, microbes, water soluble molecules, insoluble organic molecules, or mixtures thereof.

6. The method according to claim 1, wherein the draw solution is formed by dissolving phase-separated thermo-responsive draw solute.

7. A method for water desalination and purification using a thermo-responsive draw solute for forward osmosis, the method comprising:
1) bringing unpurified water into contact with a draw solution comprising the thermo-responsive draw solute at a higher concentration than the unpurified water through a semi-permeable membrane;
2) allowing clean water to flow from the unpurified water into the draw solution through the semi-permeable membrane by forward osmosis;
3) adjusting the temperature of the draw solution to or below the critical solution temperature of the thermo-responsive draw solute to cause an upper critical solution temperature (UCST) phase separation of the thermo-responsive draw solute from the draw solution; and
4) separating the clean water from the thermo-responsive draw solution.

8. The method according to claim 7, wherein the thermo-responsive draw solute has a molar mass of 50 to 3000 g/mol and undergoes an UCST phase transition at a temperature of 0° C. to 70° C.

9. The method according to claim 7, wherein the thermo-responsive draw solute is selected from the group consisting of:

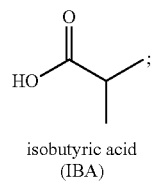
isobutyric acid (IBA)

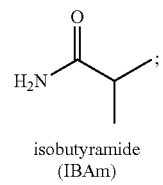
isobutyramide (IBAm)

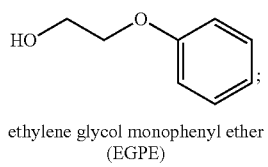
ethylene glycol monophenyl ether (EGPE)

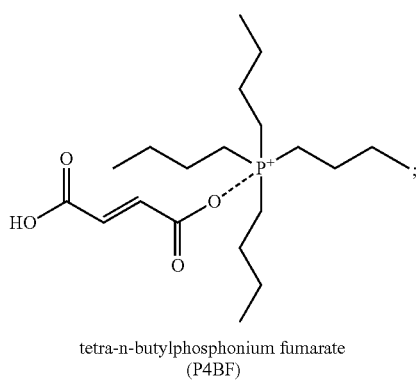
tetra-n-butylphosphonium fumarate (P4BF)

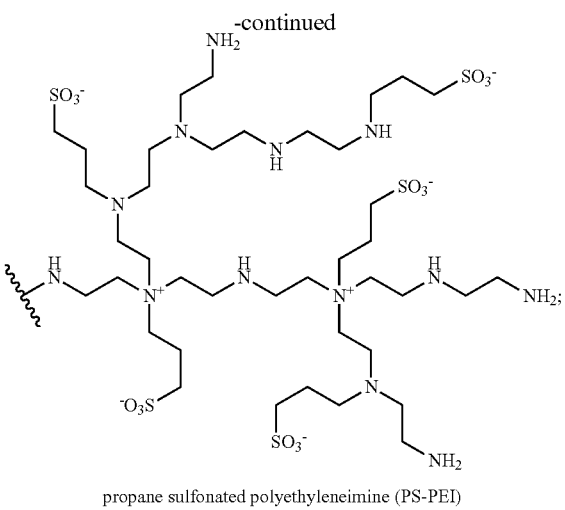
propane sulfonated polyethyleneimine (PS-PEI)

and mixtures thereof.

10. The method according to claim 7, wherein the semi-permeable membrane is a cellulose acetate or polyether sulfone semi-permeable membrane.

11. The method according to claim 7, wherein the unpurified water is water comprising ions, colloids, microbes, water soluble molecules, insoluble organic molecules, or mixtures thereof.

12. The method according to claim 7, wherein the draw solution is formed by dissolving phase-separated thermo-responsive draw solute.

13. A method for water desalination and purification using a thermo-responsive draw solute for forward osmosis, the method comprising:
1) bringing unpurified water into contact with a draw solution comprising the thermo-responsive draw solute at a higher concentration than the unpurified water through a semi-permeable membrane;
2) allowing clean water to flow from the unpurified water into the draw solution through the semi-permeable membrane by forward osmosis;
3) adjusting the temperature of the draw solution to or below the critical solution temperature of the thermo-responsive draw solute to cause a phase transition of the thermo-responsive draw solute from the draw solution; and
4) separating the clean water from the draw solution,
wherein the thermo-responsive draw solute is selected from the group consisting of:

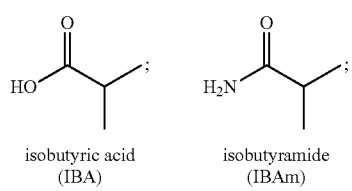
isobutyric acid (IBA)   isobutyramide (IBAm)

-continued
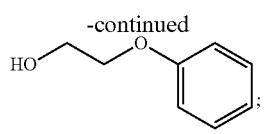
ethylene glycol monophenyl ether
(EGPE)
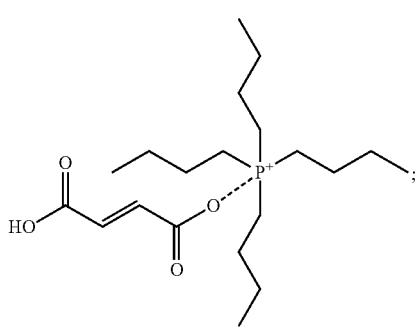
tetra-n-butylphosphonium fumarate
(P4BF)
-continued
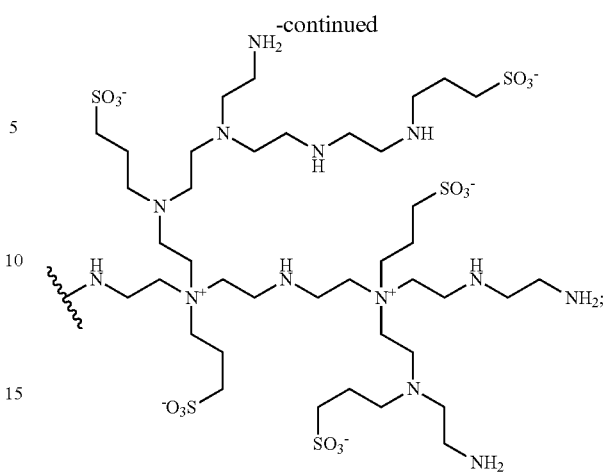
propane sulfonated polyethyleneimine (PS-PEI)
and mixtures thereof.
14. The method according to claim 13, wherein the phase transition in element 3) results in phase separation of the thermo-responsive draw solute.
* * * * *